United States Patent
Soni et al.

(10) Patent No.: US 9,465,917 B2
(45) Date of Patent: Oct. 11, 2016

(54) HAZARD BASED ASSESSMENT PATTERNS

(71) Applicant: Roche Diagnostics Operations, Inc., Indianapolis, IN (US)

(72) Inventors: Abhishek Soni, Indianapolis, IN (US); David L. Duke, Fishers, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 319 days.

(21) Appl. No.: 14/291,446

(22) Filed: May 30, 2014

(65) Prior Publication Data

US 2015/0347698 A1 Dec. 3, 2015

(51) Int. Cl.
- G06F 17/00 (2006.01)
- G06F 17/20 (2006.01)
- G06F 19/00 (2011.01)
- G06N 5/04 (2006.01)

(52) U.S. Cl.
CPC ............. *G06F 19/345* (2013.01); *G06N 5/047* (2013.01)

(58) Field of Classification Search
USPC .......................................................... 706/11
See application file for complete search history.

(56) References Cited

U.S. PATENT DOCUMENTS

| | | | |
|---|---|---|---|
| 4,660,151 A | 4/1987 | Chipman et al. | |
| 5,339,826 A | 8/1994 | Schmidt et al. | |
| 8,532,933 B2* | 9/2013 | Duke | G06F 19/345 702/19 |
| 8,589,106 B2* | 11/2013 | Engelhardt | A61B 5/14532 600/347 |
| 8,755,938 B2* | 6/2014 | Weinert | G06F 19/3456 600/365 |
| 8,801,005 B1* | 8/2014 | Flickner | B62B 3/04 280/35 |
| 8,843,321 B2* | 9/2014 | Duke | A61B 5/14532 702/19 |
| 9,326,709 B2* | 5/2016 | Budiman | A61B 5/14532 |
| 2004/0127777 A1 | 7/2004 | Ruchti et al. | |
| 2004/0162678 A1 | 8/2004 | Hetzel et al. | |
| 2007/0179367 A1 | 8/2007 | Ruchti et al. | |
| 2008/0073443 A1 | 3/2008 | Tollens et al. | |
| 2008/0154513 A1 | 6/2008 | Kovatchev et al. | |
| 2010/0075353 A1 | 3/2010 | Heaton | |
| 2011/0237918 A1 | 9/2011 | Wagner et al. | |
| 2012/0215085 A1 | 8/2012 | Werner et al. | |
| 2013/0109944 A1 | 5/2013 | Sparacino et al. | |

FOREIGN PATENT DOCUMENTS

| | | | |
|---|---|---|---|
| EP | 1918837 A1 | 5/2008 | |
| WO | 01/13786 A1 | 3/2001 | |

(Continued)

OTHER PUBLICATIONS

A portable non-invasive blood glucose monitoring device R. A. Buda; M. Mohd. Addi Biomedical Engineering and Sciences (IECBES), 2014 IEEE Conference on Year: 2014 pp. 964-969, DOI: 10.1109/IECBES.2014.7047655 IEEE Conference Publications.*

(Continued)

*Primary Examiner* — Michael B Holmes
(74) *Attorney, Agent, or Firm* — Dinsmore & Shohl LLP

(57) ABSTRACT

Methods and devices for retrospectively assessing continuous monitoring reference pattern data to determine a risk of a patient glucose level measurement taken in at least one data segment being outside a predetermined range. The methods and devices can include executing an algorithm to compare risk scores derived from reference pattern data in a currently collected data segment with risk scores of previously stored reference pattern data of previously collected data segments for a patient for assessing risk.

20 Claims, 20 Drawing Sheets

(56) References Cited

FOREIGN PATENT DOCUMENTS

| WO | 2004043230 A2 | 5/2004 |
|----|---------------|--------|
| WO | 2010075350 A1 | 7/2010 |

OTHER PUBLICATIONS

A stochastic model to assess the variability of blood glucose time series in diabetic patients self-monitoring P. Magni; R. Bellazzi IEEE Transactions on Biomedical Engineering Year: 2006, vol. 53, Issue: 6 pp. 977-985, DOI: 10.1109/TBME.2006.873388 IEEE Journals & Magazines.*

Development of urine glucose level monitor for home healthcare using near infrared spectroscopy Shinobu Tanaka; Mitsuhiro Ogawa; Tao Gu; Ken-ichi Yamakoshi BioInformatics and BioEngineering, 2008. BIBE 2008. 8th IEEE International Conference on Year: 2008 pp. 1-3, DOI: 10.1109/BIBE.2008.4696829 IEEE Conference Publications.*

Prediction of glucose concentration in type 1 diabetic patients using support vector regression Eleni I. Georga; Vasilios C. Protopappas; Demosthenes Polyzos Proceedings of the 10th IEEE International Conference on Information Technology and Applications in Biomedicine Year: 2010 pp. 1-4, DOI: 10.1109/ITAB.2010.5687764.*

Clarke, et al., "Statistical Tools to Analyze Continuous Glucose Monitor Data", Diabetes Technology & Therapeutics, vol. 11, Suppl. 1, 2009; p. S-45-S-54.

Cobelli, et al., "Diabetes: Models, Signals and Control", IEEE Reviews in Biomedical Engineering, vol. 2, 2009; p. 54-96.

Palerm, et al., "Hypoglycemia Detection and Prediction Using Continuous Glucose Monitoring—A Study on Hypoglycemic Clamp Data", Journal of Diabetes Science and Technology; vol. 1, Issue 5, Sep. 2007, p. 624-629.

Cameron, Fraser, et al., "A Closed Loop Artificial Pancreas Based on Risk Management", Journal of Diabetes Science and Technology: vol. 5, issue 2, Mar. 2011, pp. 368-379.

Kovatchev, Boris, et al., "Symmetrization of the Blood Glucose Measurement Scale and Its Applications", Diabetes Care: vol. 20, No. 11, Nov. 1997, pp. 1655-1658.

Guerra, Stefania, et al., "A Dynamic Risk Measure from Continuous Glucose Monitoring Data", Diabetes Technology & Therapeutics, vol. 13, No. 8, 2011, pp. 843-853.

Bentley, "Multidimensional Binary Search Trees Used for Associative Searching," ACM, vol. 18, No. 9, Sep. 1975, p. 509-517, USA.

Bentley, "Multidimensional Divide-And-Conquer," ACM, vol. 23, No. 4, Apr. 1980, p. 214-229, USA.

International Search Report dated Aug. 21, 2015 pertaining to International application No. PCT/US2015/31965.

\* cited by examiner

| Name | Shape | Cluster Size |
|---|---|---|
| Cluster 1 |  | 284 |
| Cluster 2 |  | 1035 |
| Cluster 3 |  | 632 |
| Cluster 4 |  | 327 |
| Cluster 5 |  | 808 |

HAZARD BASED ASSESSMENT PATTERNS

TECHNICAL FIELD

This disclosure relates to methods and devices for retrospectively assessing continuous monitoring reference pattern data. The assessment can be to determine a risk of a patient glucose level measurement taken in at least one data segment being outside a predetermined range. The methods and devices can include executing an algorithm to compare risk scores derived from reference pattern data in a currently collected data segment with risk scores of previously stored reference pattern data of previously collected data segments for a patient for assessing risk.

BACKGROUND

Diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep the glucose levels at an optimum level. Healthcare may involve both establishing a therapeutic program and monitoring the progress of the afflicted person. Monitoring blood glucose levels is an important process that is used to help diabetics maintain blood glucose levels as near as normal as possible throughout the day. Monitoring can also allow successful treatment of a diabetic by altering therapy as necessary. Monitoring may allow the diabetic to monitor more closely his or her condition and, in addition, can provide information of value to the healthcare provider in determining both progress of the patient and detecting any need to change the patient's therapy program.

Advances in the field of electronics over the past several years have brought about significant changes in medical diagnostic and monitoring equipment, including self-care monitoring. In controlling and monitoring diabetes, relatively inexpensive and easy-to-use blood glucose monitoring systems have become available that provide reliable information that allows a diabetic and his or her healthcare professional to establish, monitor and adjust a treatment plan.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a non-continuous system may require a diabetic to apply a blood sample to reagent-impregnated region of a test strip, wipe the blood sample from the test strip after a predetermined period of time, and determine blood glucose level by comparing the color of the reagent-impregnated regions of the test strip with a color chart supplied by the test strip manufacturer. These systems also can rely on lancing and manipulation of the fingers or alternate blood draw sites, which can be extremely painful and inconvenient, particularly for children.

An example of a continuous system is a continuous glucose monitors ("CGM") that can be implanted subcutaneously and measure glucose levels in the interstitial fluid at various periods throughout the day, providing data that shows trends in glucose measurements over a period of time. CGMs can provide large quantities of data that need to be processed to find similar data. The data can be used to identify harmful patient behaviors or to help optimize therapy based on similar past experiences. It can also be used to monitor glucose over time to determine a blood sugar pattern. Because of the large quantities of data involved, an efficient algorithm may be needed to enable pattern matching on devices with limited processing power.

SUMMARY

Specific embodiments provided herein describe a method for retrospectively assessing continuous monitoring reference pattern data to determine a risk of a patient glucose level measurement taken in at least one data segment being outside a predetermined range comprising: providing: a physiological data input device for acquiring data of the at least one data segment, wherein the data is in the form of at least one glucose level measurement; a controller in communication with the physiological data input device for generating a reference pattern from the data; a memory coupled to the physiological data input device and the controller for storing reference pattern data of the at least one data segment and for storing an algorithm to compute and assign a risk score for the reference pattern data of the at least one data segment and access a database containing previously stored reference pattern data of previously collected data segments with previously assigned risk scores; a processor in communication with the memory in order to execute the algorithm to compute and to assign the risk score computed for the reference pattern data of the at least one data segment and access the database containing the previously collected data segment reference pattern data with the assigned risk scores; collecting the data of the at least one data segment; generating the reference pattern from the data; storing the reference pattern data; executing, via the processor, the algorithm to compute and assign the risk score for the reference pattern data of the at least one data segment; and comparing the risk score to the previously assigned risk scores of the reference pattern data of the previously acquired data segments for a patient for the retrospective assessment of the risk of the patient glucose level measurement taken in the at least one data segment being outside the predetermined range.

Additional specific embodiments provided herein describe method of risk quantification in one or more physiological reference pattern data of a subject to identify potential trouble spots in one or more regions of the reference pattern data where therapy change can be employed by a health care professional, said method comprising: providing: a physiological data input device for acquiring data of at least one data segment, wherein the data is in the form of at least one glucose level measurement; a controller in communication with the physiological data input device to for generating a reference pattern from the data; a memory coupled to the physiological data input device and the controller for storing reference pattern data of the at least one data segment and for storing an algorithm to compute and assign a risk score for the reference pattern data of the at least one data segment and access a database containing previously stored reference pattern data of previously collected data segments with previously assigned risk scores; a processor in communication with the memory to execute the algorithm to compute and to assign the risk score computed for the reference pattern data of the at least one data segment and access the database containing the previously collected data segment reference pattern data and the previously assigned risk scores; collecting, via the physiological data input device, the data in the at least one data segment obtained during continuous monitoring; generating, via the controller, the reference pattern of the data of the at least one data segment; storing, via the memory, the reference pattern data of the at least one data segment; executing, via the processor, the algorithm; assigning, via the algorithm, the risk score computed for the reference pattern data of the at least one data segment; accessing, via the algorithm, the database containing the stored reference pattern data with the previously assigned risk scores; comparing, via the algorithm, the risk score of the collected data of the at least one data segment with the previously assigned risk scores of the database; identifying, via the algorithm, the data segments stored in the database with the same risk score as the risk score computed for the reference pattern data of the at least one data segment for identification of the potential trouble spots in the one or more regions of the reference pattern data where the therapy change can be employed by the health care professional; sending the risk score computed for the reference pattern data of the data segment and a list of the identified data segments stored in the database with the same risk score as the risk score to the heath care professional.

Additional specific embodiments provided herein describe device for retrospectively assessing continuous monitoring reference patterns to determine a risk of a patient glucose level measurement taken in at least one data segment being outside a predetermined range comprising: a physiological data input device for acquiring data of the at least one data segment; a controller in communication with the physiological data input device to for generating a reference pattern from the data; a memory coupled to the physiological data input device and the controller for storing the reference pattern data of the at least one data segment; and a processor in communication with the memory and configured to execute an algorithm, stored in the memory, to assign a risk score computed for the reference pattern data of the at least one data segment and access a database containing stored reference pattern data with previously assigned risk scores to compare the risk score with the previously assigned risk scores and determine a therapy to decrease a future risk score.

Figure 1:
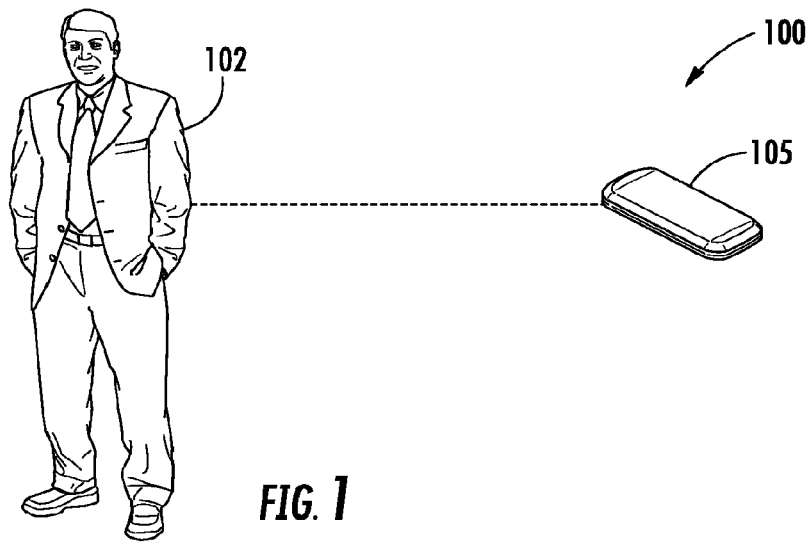
FIG. 1 depicts a diagram of an exemplary version of a patient monitoring system associated with a diabetic patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

There is a problem in the medical field of how to quickly assess patient risk based in part on a patient's blood glucose levels or changes in those levels. Specifically, there is a need for medical personnel to be able to, upon seeing a patient, quickly assess patient risk to adverse events from non-homeostatic levels of glucose or changes in glucose levels that can lead to adverse events. Embodiments described herein make is easy for medical personnel to very quickly assess continuous monitoring (CM) and quickly distinguish which curves represent a high risk to the patient. Embodiments can enable a quick assessment of past glycemic behavior, identify trouble spots, and help in therapy adjustment and/or optimization. The needs are met by computing risk scores for each of the pattern data of the data that are stored in a database, and finding matches that have a similar risk score.

The concept of pattern matching has been presented in U.S. application Ser. No. 12/975,654, "Patient Monitoring System with Efficient Pattern Matching Algorithm," however Ser. No. 12/975,654 discusses only how the patterns are obtained, it is not easy or evident from the patterns what patterns represent the most risk. Also, the concept of clustering has been presented in U.S. application Ser. No. 13/912,318, "A Method of Screening for Disorders of Glucose Metabolism," however Ser. No. 13/912,318 assigns data segments to clusters but does not describe methods for assessing the risk associated with a cluster. Additionally, the concept pertaining to the computation of risk and mapping of risk surface has been presented in U.S. application Ser. No. 13/645,198, "System and Method for Assessing Risk Associated with a Glucose State," however Ser. No. 13/912, 318 does not discuss risk in the context of patterns. Regarding U.S. patent application Ser. Nos. 12/975,654, 13/912, 318, and 13/645,198, the entire disclosures of each of the applications are fully herein incorporated by reference. Therefore, further improvements are needed. The current application provides further improvements of U.S. patent application Ser. No. 12/975,654, as detailed herein.

Embodiment described herein provide for advantages over prior approaches. Aspects of the current application allow a user, patient, or medical personnel to hone in very quickly on potential trouble spots, and allows the quantification of risk for matched patterns thus allowing a numerical comparison. It also provides a starting point to assess and evaluate regions where therapy change can be employed to decrease risk.

Current embodiments provide for retrospectively assessing continuous monitoring reference patterns to quickly assess patient risk based in part on a patient's blood glucose levels or changes in those levels.

Example Devices and Methods

FIG. 1 depicts an exemplary configuration of a patient monitoring system 100 in association with a patient 102. The patient 102 may be a diabetic patient, or a patient with a physiological condition which requires routine or continuous monitoring. The patient monitoring system 100 comprises hardware and software components that may be utilized for implementing a reference pattern data matching feature as described further herein. As illustrated, the patient monitoring system 100 comprises a device 105. Device 105 may be a handheld system with limited processing power, such as a PDA, mobile phone, glucose meter, etc. Device 105 may also be a personal computer. As further shown in FIG. 2, device 105 may comprise a physiological data input device(s) 110, a data interface 115, a processor 120, a database 130, a memory 135 along with analysis logic 132, and a display 140. These components are "operably connected" to each other, which may include one or more components connected to one or more other components, either directly or through one or more intermediate components such that they may communicate and pass information as needed to perform at least the hereinafter described processes and functions. The connection may be mechanical, electrical connection, or a connection that allows transmission of signals between the components, e.g., wired or wirelessly. The device 105 may further include an input mechanism or user interface 145 to input information and/or make data/output requests. Exemplary input mechanisms or user interfaces 145 may include a touch screen, input buttons, a keyboard, a mouse, a microphone, and combinations thereof. In one embodiment, the patient monitoring system 100 enables continuous glucose monitoring in which device 105 is operable to take multiple measurements of a concentration of glucose or a substance indicative of the concentration or presence of glucose via the physiological data input device 110, and process that dataset using the processor 120 to find similar pattern data. As used herein, continuous (or continual) glucose monitor (or monitoring) may include the period in which monitoring of glucose concentration is continuously, continually, and/or intermittently (e.g., regularly or irregularly) performed.

As used herein, "meal components" describes a part/portion of a meal, and can be used with tagged data to describe what a user/patient has, is, will be eating/plans on eating.

In specific embodiments the software/firmware code contains instructions that, when executed by the processor of a computing device, causes computing device to perform functions as described herein. Computing devices may alternatively include one or more application-specific integrated circuits (ASICs), field-programmable gate arrays (FPGAs), digital signal processors (DSPs), hardwired logic, or combinations thereof. While an example computing device is illustratively a glucose monitor, other suitable computing devices may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Multiple computing devices may be used together to perform the functions of computing device described herein.

Figure 2:
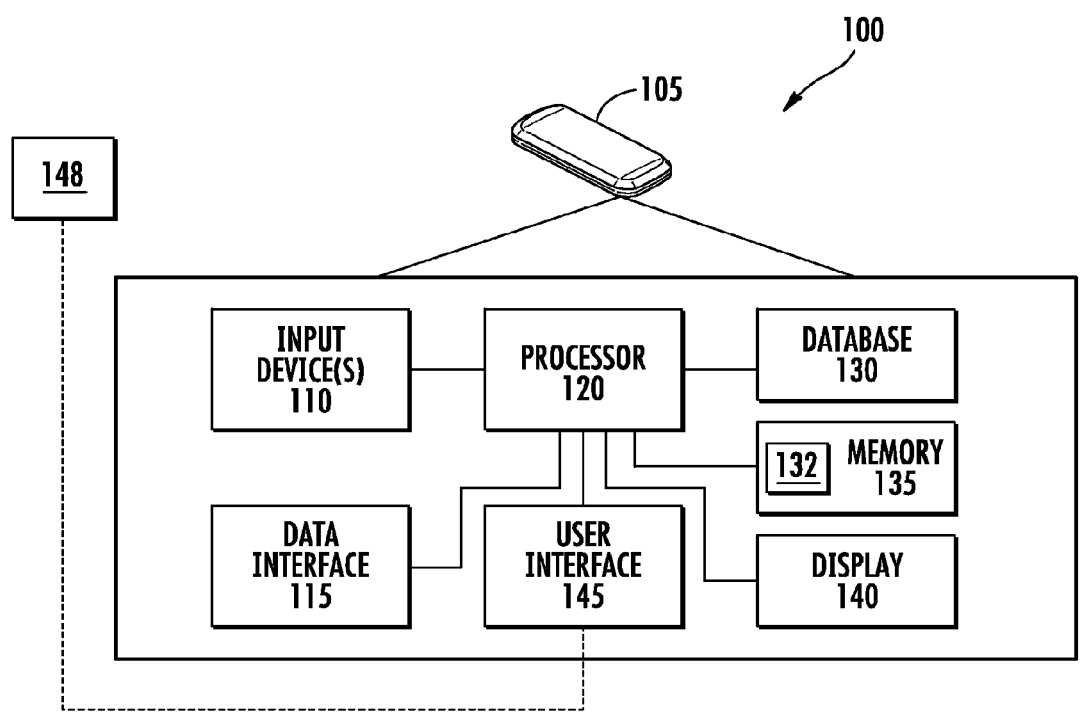
FIG. 2 depicts a block diagram of the exemplary version of the patient monitoring system of FIG. 1.

Referring to FIG. 2, the physiological data input device 110 may be, e.g., in one embodiment one or more sensors which gather automatically patient-specific physiological data such as, e.g., blood glucose, blood viscosity or other information concerning the blood chemistry of the patient 102, physical activity, temperature, heart rate, blood pressure, breathing pattern, other patient-specific physiological parameters, and combinations thereof. In one embodiment, the physiological data input device 110 can be a component or region of a patient monitoring system 100 by which glucose can be quantified and configured to produce a signal indicative of a glucose concentration of the patient 102. In operation, the physiological data input device 110 may by a glucose sensor which measures and acquires a detectable signal (e.g., a chemical signal, electrochemical signal, etc.), either directly or indirectly, from glucose or derivatives thereof that are indicative of the concentration or presence of glucose and then may transmit the signal to the processor 120 for further processing and/or storage in database 130. The physiological data input device 110 may be in communication with processor 120.

As used herein, the physiological data input device 110 may be a continuous device, for example, a subcutaneous, transdermal (e.g., transcutaneous), or intravascular device. However, it should be understood that the devices and methods described herein can be applied to any device (including external devices) capable of detecting a concentration of glucose and providing an output signal that represents the concentration of glucose. The physiological data input device 110 in another embodiment can be hardware and/or software which can analyze a plurality of intermittent biological samples, for example, blood, interstitial fluid, other desired biological fluid, etc. The physiological data input device 110 can use any method of glucose-sensing, including enzymatic, chemical, physical, electrochemical, spectrophotometric, polarimetric, calorimetric, radiometric, etc. The physiological data input device 110 may use any method, including invasive, minimally invasive, and non-invasive sensing techniques, to provide an output signal indicative of, e.g., the glucose concentration or other physiological data. The output signal can be a raw data measurement that is used to provide a useful value of glucose to a user, such as a patient or physician, who may be using the device. Smoothing, evaluation methods, etc. may be applied to the raw data measurement to provide transformed data measurements to the user.

Data measurements may be derived from the intermittent collection of data comprising measurements made by a device, such as e.g., the physiological data input device 110, (for example, a current measurement that ultimately corresponds to a glucose amount or concentration). The data measurements may be further associated with relevant data tags (also called herein "tagging"). By way of example only, a data tag may include when a meal was eaten, insulin was given, exercise took place, etc. Additionally, a data tag may include the amount of nutritional content in a meal, insulin, oral medication, exercise, etc. The data measurements may further comprise determining transformed data measurements from one or more raw data measurements and associating those transformed data measurements with relevant data tags.

The data measurements are obtained from a particular biological system (e.g., blood, interstitial fluid, etc.) using a device, such as e.g., the physiological data input device 110, maintained in operative contact with the biological system over a time window, also herein referred to as a data segment. The time window may be a defined period of time (e.g., hour(s), day(s), etc.) to obtain a series of data measurements (e.g., second(s), minute(s), hour(s), etc.) resulting in at least one time window dataset. The time window may be started and stopped by the patient 102 as well. By way of example only, the patient 102 may start the time window at the beginning of a meal and stop the time window at some later date after the meal. The at least one time window data set (or data measurements) may be collected from a single individual. Alternatively, the at least one time window data set (or data measurements) may be collected from multiple individuals and compiled into a database, at either the time the at least one time window data set (or data measurements) were collected or subsequently. The at least one time window data set may include raw data measurements, transformed data measurements, raw or transformed data measurements associated with data tags, or a combination thereof from the sensor.

The physiological data input device 110 may be capable of measuring only glucose in one embodiment. Alternately, in other embodiments, the physiological data input device 110 may be capable of measuring any other physiological analyte of interest that is a specific substance or component that is being detected and/or measured by chemical, physical, enzymatic, or optical analysis. The data measurements for each physiological analyte is collected and compiled into a multi-analyte database such as, e.g., database 130. In another example, the database 130 can also be formulated by compiling data measurements collected using multiple monitors, each of which measures a single substance, resulting in the multi-analyte database.

Examples of physiological analytes can include any specific substance, component, or combinations thereof that one is desirous of detecting and/or measuring in a chemical, physical, enzymatic, or optical analysis. Such physiological analytes include, but are not limited to, urate/uric acid, glucose, urea (blood urea nitrogen), lactate and/or lactic acid, hydroxybutyrate, cholesterol, triglycerides, creatine, creatinine, insulin, hematocrit, and hemoglobin), carbonate, calcium, potassium, sodium, chloride, bicarbonate, blood gases (e.g., carbon dioxide, oxygen, etc.), heavy metals (e.g., lead, copper, etc.), lipids, amino acids, enzyme substrates or products indicating a disease state or condition, other markers of disease states or conditions, etc. In the case of multi-analyte data databases, all of the physiological analytes may be related to a single physiologic state or condition; alternatively, in other embodiments, each physiological analyte may be relevant to a different physiological state or condition.

In still other embodiments, one or more of the above described physiological data/information may be entered manually by the patient 102, as well as requested for output (e.g., displayed on display 140, sent to another external device via data interface 115, etc.), via the user interface 145. In still other embodiments, the input device 110 may also include, for example, a controller, microcontroller, processor, microprocessor, etc. that is configured to receive and/or process signals, communicate with processor 120, and generate a reference pattern. The reference pattern can be the most recent data set (e.g., the most recent at least one time window data set gathered by the input device 110, a data set from the current day, hour(s), minute(s), etc. provided in memory 135 and/or database 130) and/or for any other data set of interest, e.g., historical data (previous day(s), week(s), month(s), year(s), etc.) of the patient 102. The data set can be provided from the input device 110, the database 130, the memory 135, the user interface 145, and/or from any another external source of patient data that the device 105 may communicate with via the data interface 115. It is to be appreciated that as such the reference pattern can be generated from any of the data available to the device 105, and by any method performed by the processor 120, the input device 110 (if provided with processing means), or an external device(s) operating on the data (and provided to the device via the data interface 115), in which to provide a pattern of interest, such as e.g., a glucose curve. Exemplary methods for generating a glucose curve may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The reference pattern can also be generated from data resulting from a query inputted via the user interface 145 and run by the processor 120 on recent data gathered by the input device 110 or stored data provided in database 130, memory 135 and/or in other external sources that were queried by the processor 120 via data interface 115. The reference pattern may also include any relevant data tags or multi-analyte data, and the generated and/or received reference pattern may be stored in the database 130 and/or memory 135 until needed by the processor 120 for a pattern matching process discussed hereafter in a later section.

The data interface 115 may be hardware and/or software which provides the device 105 with the ability to communicate wired and/or wirelessly with other devices and components as discussed hereafter in some embodiments, as well as to read from and write to non-transitory computer-readable products or storage medium, such as non-transitory computer-readable medium 148, in other embodiments. For the purposes of this description, a non-transitory computer readable product or storage medium can be any apparatus that can contain or store, programs and/or code for use by or in connection with processor, apparatus or devices.

Examples of a non-transitory computer readable product or storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Still referring to FIG. 2, the processor 120 may include any general purpose processors or any processing component configured to provide, receive and execute a sequence of instructions (such as from the memory 135). For example, processor 120 may perform calculations using at least one time window data set (or data measurements) from the physiological data input device 110 and/or the reference pattern from input device 110 (when provided with processing means), which may also be viewed as a time window data set that is generated by the input device 110. In another example, processor 120 may also compress the at least one time window data set (or data measurements) to a reduced-rank basis as will be described further herein. In another example, processor 120 may perform pattern matching with at least one time window data set (or data measurements) in a reduced-rank space as will be described further herein. Processor 120 may be implemented as a single computing device or a combination of computing devices, e.g., a combination of a digital signal processor and a microprocessor, a plurality of microprocessors, one or more microcontrollers, one or more microprocessors in conjunction with a digital signal processor core, or any other such configuration.

Still referring to FIG. 2, the display 140 may comprise a liquid crystal display ("LCD"), a touch sensitive screen, a web interface, etc. A touch screen or web interface can provide a convenient way to enter various commands and/or select various programmable options. In operation, display 140 can display information, for e.g., at least one time window data set (or data measurements), pattern match results, labeled regions to identify areas of interest, data tag information, reference patterns, etc. By way of example only, the displayed information may comprise at least one time window data set (or data measurements) that may or may not require processing by the display device prior to display. The at least one time window data set (or data measurements) displayed may be raw data, real-time data, transformed data, etc. The display 140 may comprise hardware and/or software including display instructions (e.g., software programming comprising instructions) configured to enable display of the information on display 140 and/or to obtain the information from database 130. The data in the database 130 may be queried and/or displayed by the processor 120 on the display 140.

Figure 3A:
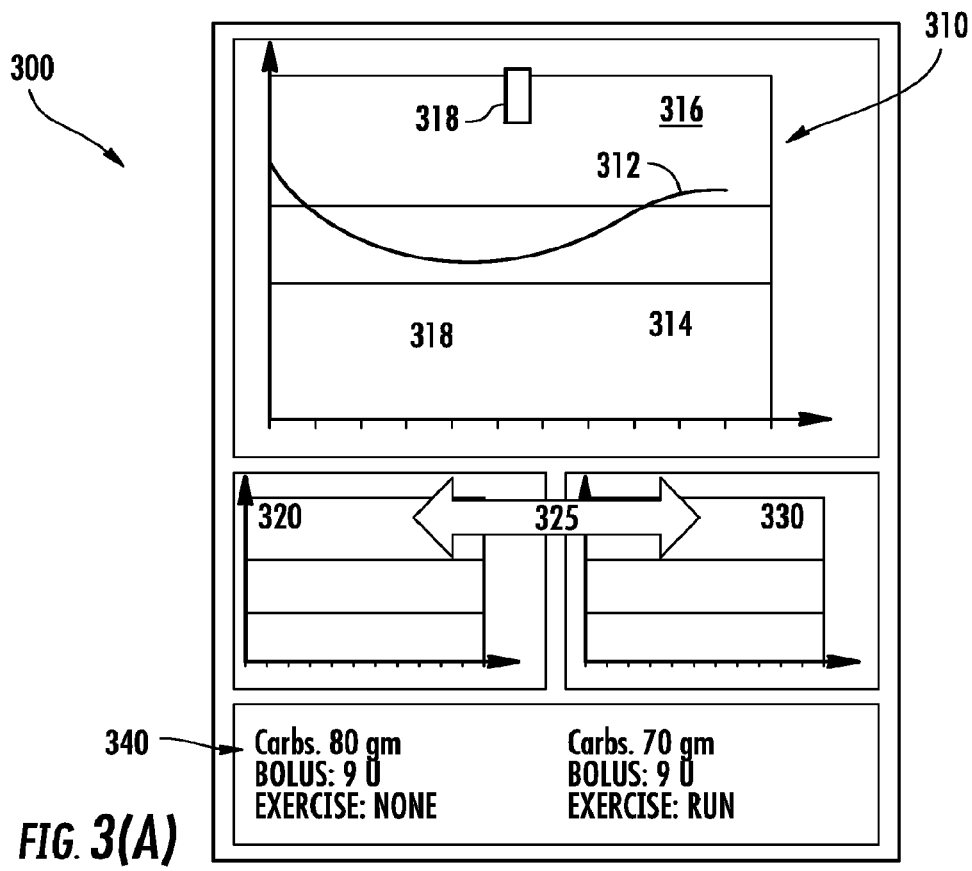
FIGS. 3(a)-3(e) depict exemplary ways of displaying various data of a pattern matching process.

Exemplary displays 140 in FIGS. 3(a)-3(e) depict various ways of displaying the different components and/or various data of a pattern-matching process. FIG. 3(a) depicts an exemplary display 300 having a reference pattern plot 310. The reference pattern plot 310 includes a plotted reference pattern 312 generated and displayed by the processor 120 from data of the patient 102 provided from the input device 110, memory 135, database 130, and/or external sources via data interface 115 as discussed previously above, which may be at least one time window data set (or data measurements) or results from a query as also discussed previously above. The reference pattern plot 310 may also include a region labeled to identify hypoglycemia 314, hyperglycemia 316, or other areas of interest. Data tags 318 may also be provided, which are shown and provide additional data relevant to the plotted reference pattern 312, for example, meal information, insulin information, exercise information, etc. Shown below reference pattern plot 310 are two pattern match plots 320, 330. Pattern match plots 320, 330 depict the closest pattern matches plotted on individual plots adjacent to reference pattern plot 310. The pattern match plots 320, 330 can be displayed by scrolling through the plots or by performing a dragging operation 325 on a touch sensitive display. The dragging operation 325 can be performed by touching the screen with a finger and then moving the finger in the desired direction on the screen. Additional data 340 can be displayed in a tabular format. The additional data 340 may be relevant to the reference pattern and match, which may include meal information, carbohydrates data, insulin dose data, exercise information, or any other data that may help in evaluating the match.

Figure 3B:
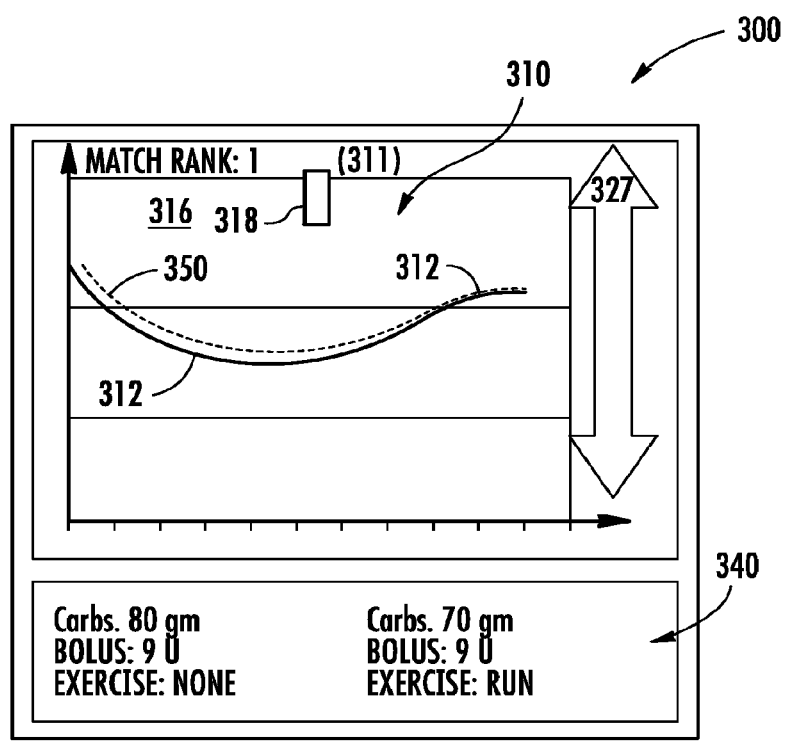

FIG. 3(b) depicts an exemplary display 300 having a reference pattern plot 310. The reference pattern plot 310 includes a plotted reference pattern 312 that may be for at least one time window data set (or data measurements) or for results of a query, and a closest pattern match plot 350 plotted on the same axis as plotted reference pattern 312. The width of the closest pattern match plot 350 and plotted reference pattern 312 are shown identical. Similar to FIG. 3(a), a hypoglycemia region 314, a hyperglycemia region 316, data tags 318 and additional data 340 are shown. Also depicted is label 311, which identifies the rank of the current match. The rank is based on how well it compares to the plotted reference pattern 312. The next closest match plot (not pictured) can be displayed by scrolling through the plots or by performing a dragging operation 327 on a touch sensitive display. The dragging operation 327 can be performed by touching the screen with a finger and then moving the finger in the desired direction on the screen.

Figure 3C:
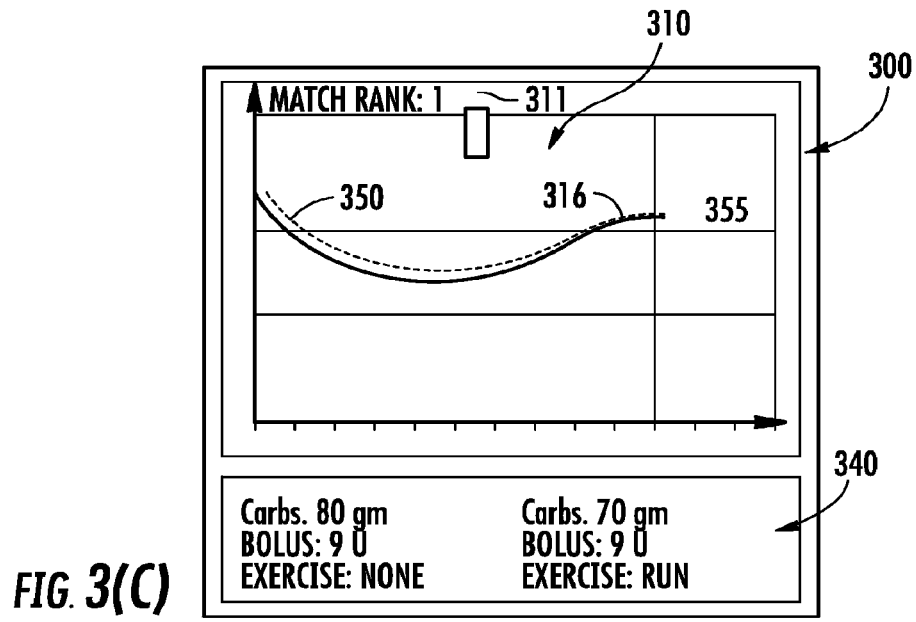

FIG. 3(c) depicts an exemplary display 300 having a reference pattern plot 310. Similar to FIG. 3(b), a hypoglycemia region 314, a hyperglycemia region 316, data tags 318 and additional data 340 are shown. As described above, the reference pattern plot 310 includes a plotted reference pattern 312 that may be for at least one time window data set (or data measurements) or for results of a query, and a closest pattern match plot 350 plotted on the same axis as the plotted reference pattern 312. The closest pattern match plot 350 may be extended to display glucose match data 355 immediately after the plotted reference pattern 312 or similarly extended to display glucose match data immediately before the plotted reference pattern 312 or both.

Figure 3D:
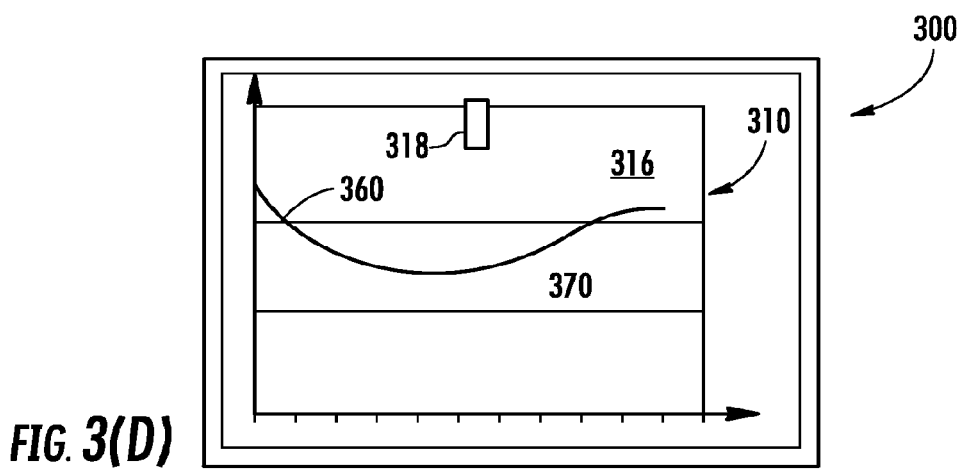

FIG. 3(d) depicts an exemplary display 300 having a raw data plot 360 and a smooth plot 370. Similar to FIG. 3(b), a hypoglycemia region 314, a hyperglycemia region 316, and data tags 318 are shown. The raw data plot 360 comprises raw, noisy data that may be at least one time window data set (or data measurements) from the sensor. The smooth plot 370 displays the compressed version of the raw data from raw data plot 360. The compressed data, which forms a smooth plot 370, may be compressed using the pattern matching or initialization algorithm described herein.

Figure 3E:
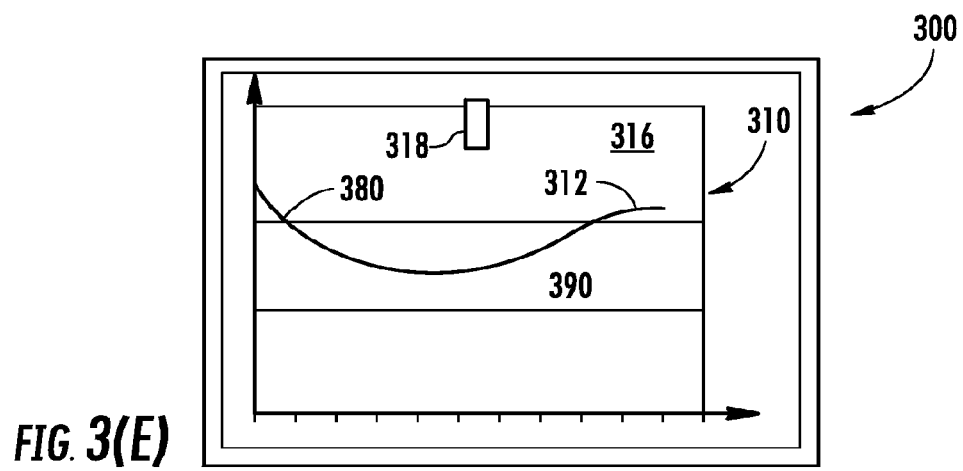

FIG. 3(e) depicts an exemplary display 300 having a reference pattern plot 310. The reference pattern plot 310 includes a plotted reference pattern 312 for data that may be for at least one time window data set (or data measurements) or for results of a query, and multiple pattern match plots 380, 390 plotted on the same axis as plotted reference pattern 312. Similar to FIG. 3(b), a hypoglycemia region 314, a hyperglycemia region 316, and data tags 318 are shown. Of course, other suitable ways in which different components of a pattern match may be depicted will be apparent to those of ordinary skill in the art in view of the teachings herein.

Referring back to FIG. 2, memory 135 may be any type of memory known in the art including, but not limited to, hard disks, magnetic tape, optical disc, semiconductor memory, a floppy diskette, a CD-ROM, a DVD-ROM, RAM memory, a remote site accessible by any known protocol, or any other memory device for storing algorithms and/or data. In operation, memory 135 may include hardware and software for compressing sensor data to a reduced-rank basis and/or for performing pattern matches, such as e.g., via included analysis logic 132. The analysis logic 132 may be suitably configured to store, interpret and process incoming information and/or to configure the processor 120 to perform such storing, interpreting, and processing of the incoming information, which, e.g., may be the at least one time window data set, raw or transformed, etc. received from the input device 110, the user interface 145, and/or resulting from a query on available data from the input device 110, the database 130, memory 135 and/or external sources via the data interface 115. As will be discussed in greater detail below, the analysis logic 132 may include a pattern-matching algorithm for performing a pattern match of a compressed dataset to past patient data in a reduced-rank space, one or more storage algorithms, one or more data pre-processing algorithm, and/or an initialization algorithm.

Referring to FIG. 2, database 130 may comprise memory capable of receiving and storing the measured and/or detected and/or identified characteristic information, e.g., at least one time window data set, raw data measurements (e.g., numeric values which correspond to a physical measurement), compressed data measurements, transformed data measurements, and may include additional related information, e.g., data tags, pointers, etc. as described above, and/or one or more storage algorithms. When the one or more storage algorithms are executed by the processor 120, it causes the processor 120 to store at least one time window data set, raw data measurements, compressed data measurements, transformed data measurements, a single numeric result calculated or derived from one or more raw data points, etc., in database 130. The processor 120 may also be caused to read at least one time window data set, raw data measurements, compressed data measurements, transformed data measurements, etc. from database 130. The processor 120 may also be caused to index the at least one time window data set, raw data measurements, compressed data measurements, transformed data measurements, etc. from the input device 110 as a function of the time and/or date. The database 130 may collect and receive data measurements automatically via the input device 110 over the window of time, thereby generating and storing the time window data set. The data may be stored in a specialized data structure format for organizing and storing data. Exemplary data structure types may include the array, the file, the record, the table, the tree, etc. The data structure may be designed to organize data to suit a specific purpose so that it can be accessed and worked with.

As noted above, the data structure of database 130 can take on a number of different forms or be structured in a variety of ways. For example, a Kd-tree (K-dimensional tree) may be used. A Kd-tree is a space-partitioning data structure similar to a binary search tree that may be useful for the rapid search and retrieval of multidimensional data. The structure is examined in detail in J. L. Bentley, "Multidimensional divide-and-conquer," *Comm. of the ACM,* 23(4), (April 1980), 214-229 and J. L. Bentley, "Multidimensional Binary Search Trees Used For Associative Searching," *Comm. of the ACM,* 18(9), 1975, which are herein incorporated by reference.

The Kd-tree splits the data having K dimensions at each node using a hyper-plane perpendicular to one of the dimensions. Each internal node has two children, representing a partition along a given dimension of the K-dimensional hyper-plane. Data may be represented in the Kd-tree by their K-dimensional compressed vector and a time parameter that links the compressed vector to a location in the saved raw data. This structure can be used to find: the nearest neighbor to a point or reference pattern, $a_r$, the nearest d neighbors, where d is the number of neighbors of interest, at least one data point within some range r of the reference pattern, $a_r$, where r is the desired distance from the reference pattern. The data structure includes standard methods for performing both n-nearest-neighbor searches and searches for similar data within a specific range that were utilized in this algorithm.

Data may further be stored in database 130 in a queue. In operation, at least one time window data set (or data measurements) received and collected from the input device 110 may be compressed using processor 120 and added to a queue. The queue contains the most recent compressed vectors waiting to be added to the kd-tree. The compressed vectors are moved from the queue to the kd-tree when they are older than N, where N is the length of the current time window. Thus, the compressed vectors are moved to the kd-tree when they are no longer overlapping with the current time window. The time windows are represented in the kd-tree by their k-dimensional compressed vector, any relevant data tags, and a time parameter that links the compressed vector to a location in the saved raw sensor data.

Figure 4:
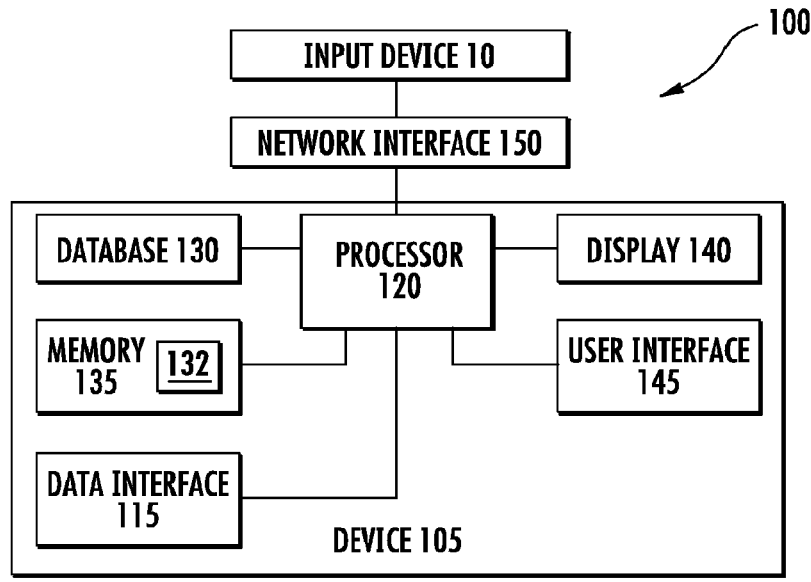
FIG. 4 depicts a block diagram of an exemplary version of a patient monitoring system.

FIG. 4 depicts another exemplary configuration of a patient monitoring system 100, and which hereafter only the difference from the configuration depicted by FIG. 2 are discussed hereafter for purposes of brevity. In this embodiment, the patient monitoring system 100 comprises device 105, input device 110 as a separate component from device 105, and a network interface 150. Device 105 comprises data interface 115, processor 120, database 130, memory 135 along with analysis logic 132, display 140, and user interface 145. The input device 110 is coupled to device 105 via the network interface 150. The network interface 150 may include a wired or wireless connection, and any wired or wireless networking hardware, such as a modem, LAN port, wireless fidelity (Wi-Fi) card, WiMax card, mobile communications hardware, and/or other hardware for communicating with other networks and/or devices. Device 105 may carry out the data storage, pattern matching and display of the results.

Figure 5:
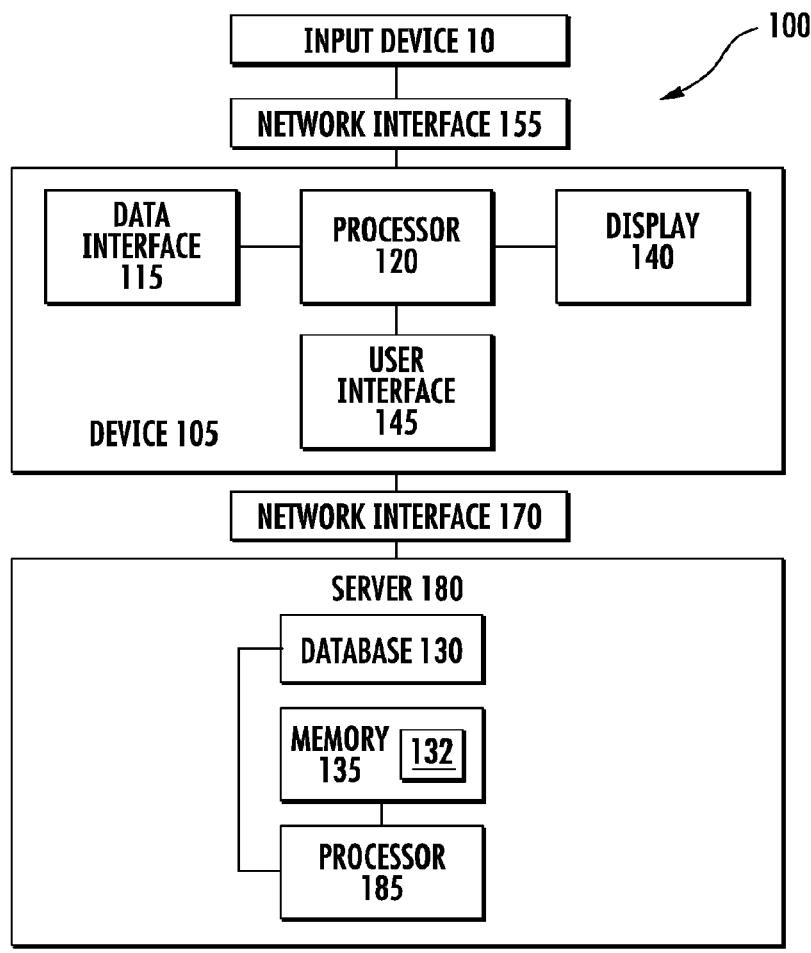
FIG. 5 depicts a block diagram of an exemplary version of a patient monitoring system.

FIG. 5 depicts another exemplary configuration of a patient monitoring system 100, and which hereafter only the difference from the configuration depicted by FIG. 4 are discussed hereafter for purposes of brevity. In this embodiment, the patient monitoring system 100 comprises device 105, the input device 110 as a separate component from device 105, a first network interface 155, a second network interface 170, and a server 180. The input device 110 may provide input to device 105 via the first network interface 155. Device 105 may be coupled to server 180 via a second network interface 170. As noted above with the network interface of FIG. 4, the first and second network interfaces may also include a wired or wireless connection, and any wired or wireless networking hardware for communicating with networks and/or devices. Device 105 comprises data interface 115, processor 120, display 140, and user interface 145. Device 105 may handle data pre-processing, inputting of data request, inputting of data queries, and display of data results. Server 180 comprises the database 130 and memory 135 along with analysis logic 132. In one example, server 180 may also comprise a processor 185 that may be configured to store data measurements into database 130 and perform pattern matching via use of the analysis logic 132.

Figure 6:
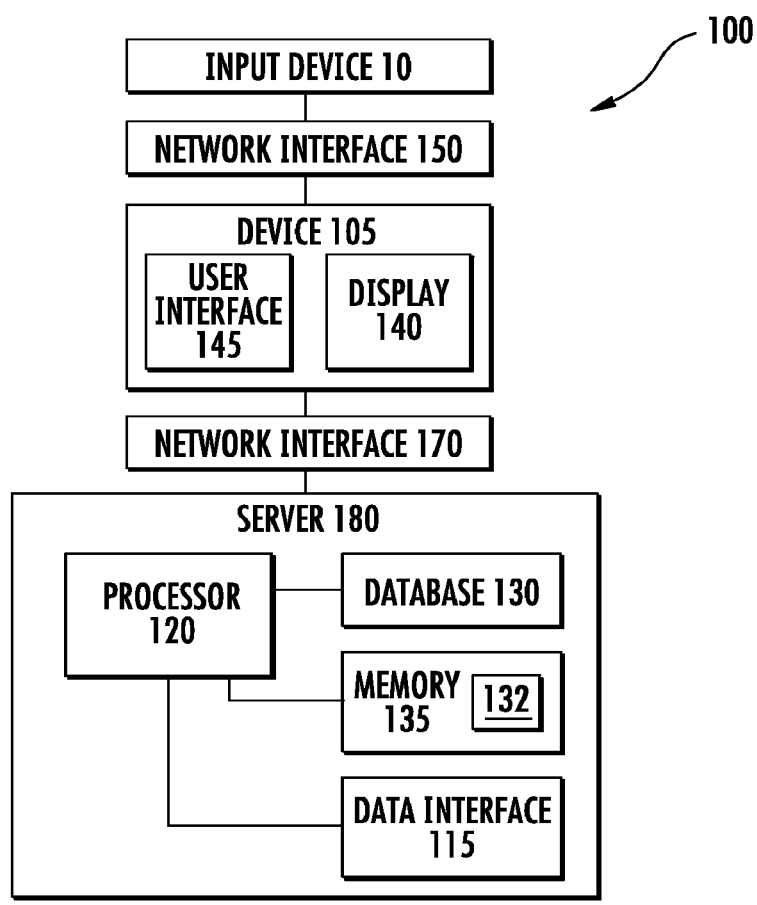
FIG. 6 depicts a block diagram of an exemplary version of a patient monitoring system.

FIG. 6 depicts another exemplary configuration of a patient monitoring system 100, and which hereafter only the difference from the configuration depicted by FIG. 5 are discussed hereafter for purposes of brevity. In this embodiment, the patient monitoring system 100 comprises device 105, input device 110 as a separate component from device 105, a first network interface 155, a second network interface 170, and a server 180. Device 105 comprises a display 140 and user interface 145, and is configured to send raw data to server 180. Server 180 comprises data interface 115, processor 120, database 130, and memory 135 along with analysis logic 132. Server 180 is configured to compress the raw data measurements, store data into database 130 and perform pattern matching.

Figure 7:
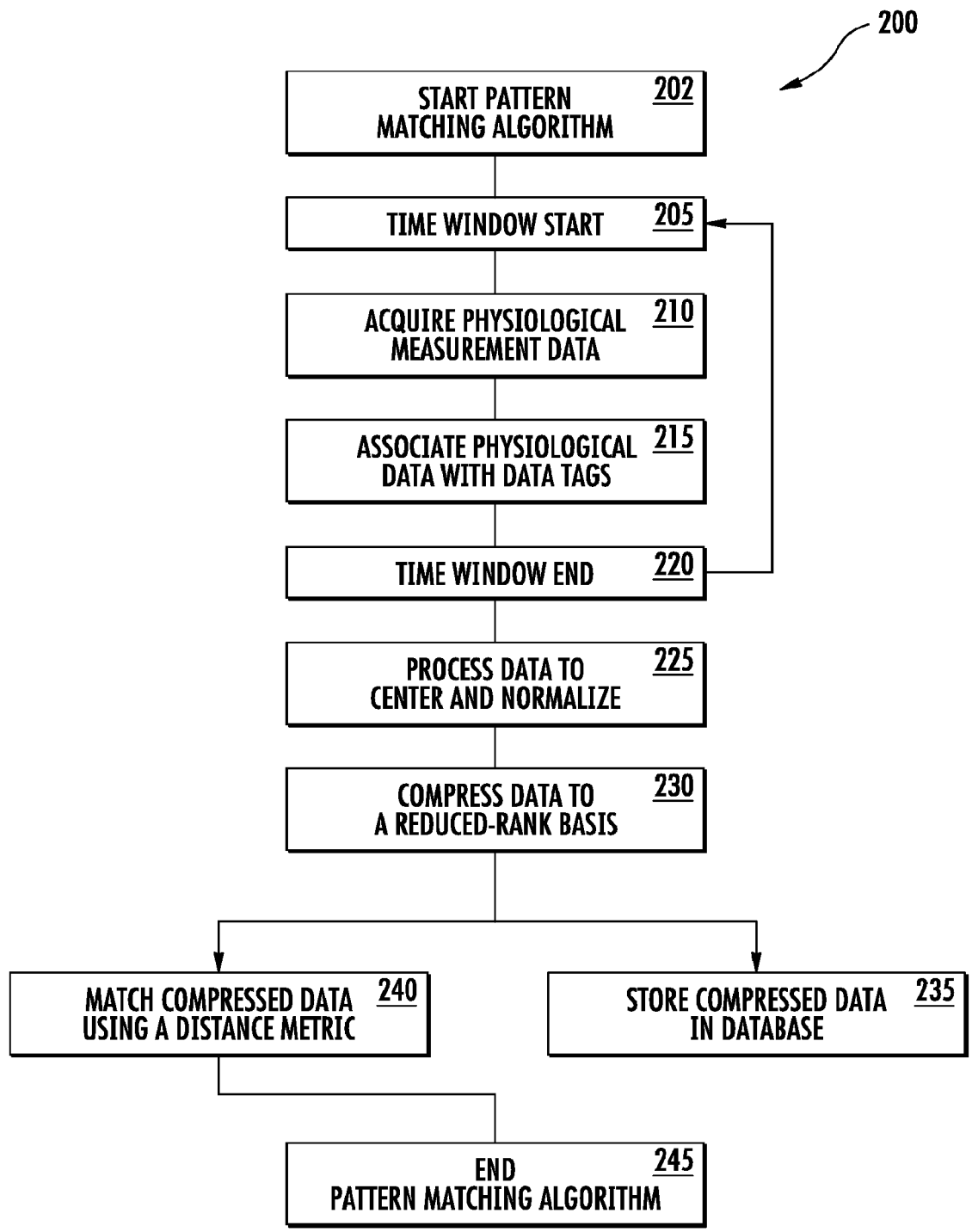
FIG. 7 depicts a flowchart of an exemplary pattern matching process using a patient monitoring system.
Figure 8:
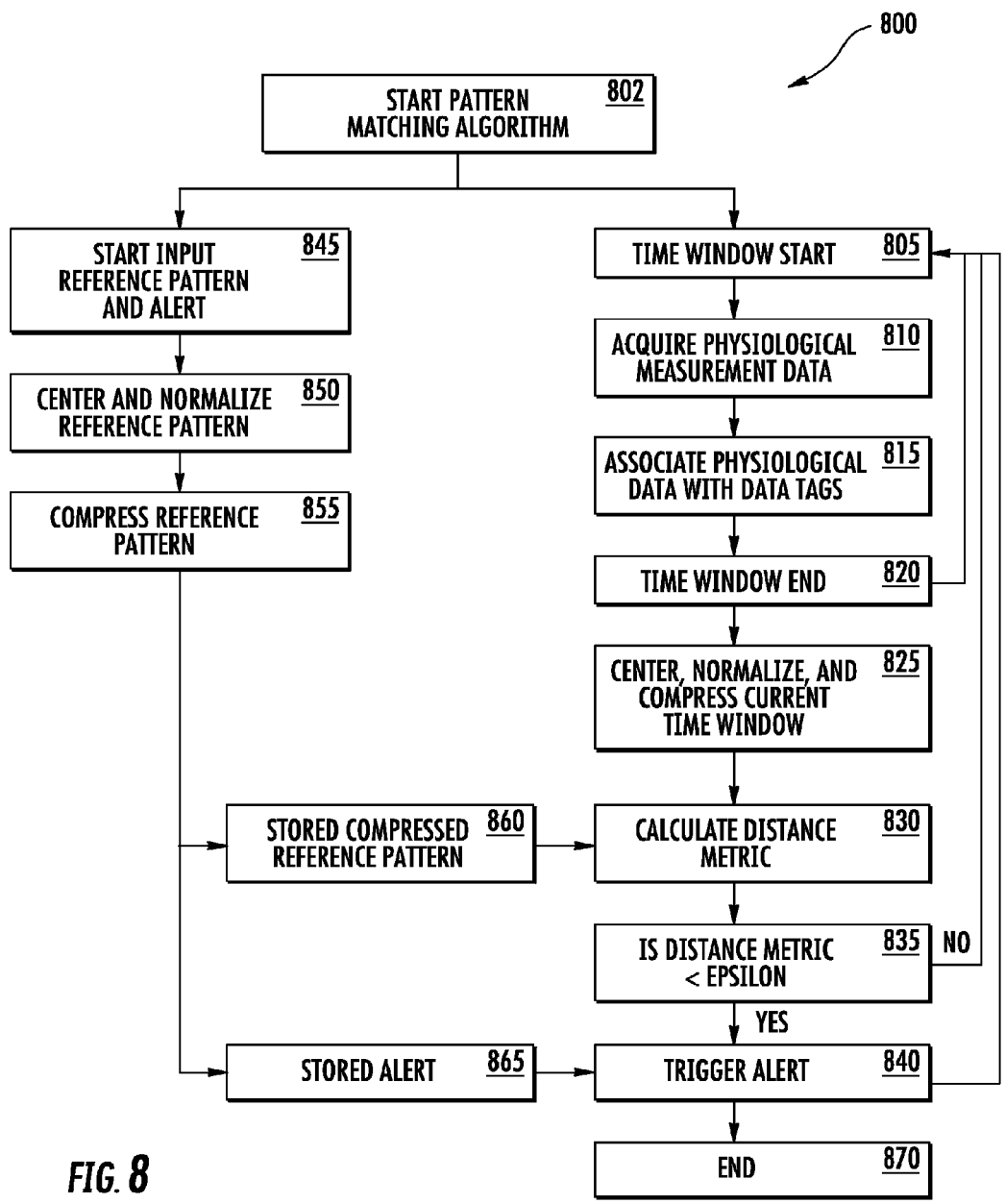
FIG. 8 depicts a flowchart of an exemplary real-time pattern matching process using a patient monitoring system.

FIGS. 7 and 8 depict flowcharts illustrating the general logic of a pattern-matching algorithm 200, 800 for efficiently finding the best match to a reference pattern. FIG. 8 depicts the general logic of a real-time pattern matching algorithm 800 for efficiently identifying a current, or most recent, time window data set that substantially matches the reference pattern. The algorithms 200, 800 are stored in a memory 135, and executed by processor 120 or 185 of the patient monitoring system 100.

Referring to FIGS. 7 and 8, blocks 202, 802 represent the start of the algorithm 200, 800. The input device 110 of a patient monitoring system 100 takes one or more glucose measurements. As noted above, other analyte and/or physiological measurements may also be taken. Blocks 205, 805 represent the start of a time window period for acquiring the one or more glucose and/or physiological measurements. The start of a time window period may be triggered by one or more of the following: user input received via the user interface 145, where the user tells the processor 120 or 185 when a new window is to begin; by a detected or scheduled event; or where a time period has elapsed and a new time period is to automatically begin.

Blocks 210, 810 represent the acquiring physiological measurement data where glucose concentration and/or other physiological data is detected by the input device 110 of the patient monitoring system 100. At least one glucose measurement, physiological measurement, or patient input, received via the user interface 145, is taken during the time window. Alternatively, a plurality of such measurements and patient input may be taken. By way of example only, measurements can be taken in increments of second, minute, hour, day, etc. Each raw data measurement is stored in database 130. Additionally, data maybe inputted by the patient 102 using the user interface 145 to answer questions displayed by the processor 120 or 185 on display 140 during the current time window period.

Blocks 215, 815 represent the association of the glucose and/or physiological measurement data with one or more data tags. As mentioned above, the data tags may include when a meal was eaten, when insulin was given, when exercise took place, the amount of nutritional content in a meal, amount of insulin, the amount and/or type of oral medication, what kind of exercise performed, etc. Of course, other data tags that can be associated with the glucose and/or physiological measurement data will be apparent to those of ordinary skill in the art in view of the teachings herein.

Blocks 220, 820 represent the end of the time window period where the processor determines whether the end has been reached. The data from the most recent time window period may be sent to a processor for further processing or alternatively may be sent to the database and held for further processing until two or more time windows of data are available. Then the two or more time windows may be further processed together. As depicted by the arrow, a new time window may be started at the end of the previous time window period, where the process for acquiring glucose and/or physiological measurement data is repeated.

Blocks 225, 825 represents the processing of data to normalize and center the data by the processor to a scale where the distribution of glucose and/or physiological measurements has a mean of zero and standard deviation of one. Blocks 230, 825 represent the compression of raw data to a reduced-rank basis performed by the processor 120. In reduced rank processing, the data may be projected on a set of basis vectors. When glucose and/or physiological measurements are correlated, a small set of basis vectors can explain most of the measurements. The input data is submitted for compression where an Eigen-decomposition is performed on the data to determine the Eigen values and Eigen vectors for the matrix $\hat{X}^T\hat{X}$. The set of K eigenvectors becomes the basis set. This set of K Eigen vectors represents the compressed equivalent of the input data. K is determined using the initialization algorithm, which is further described in FIG. 9.

Figure 9:
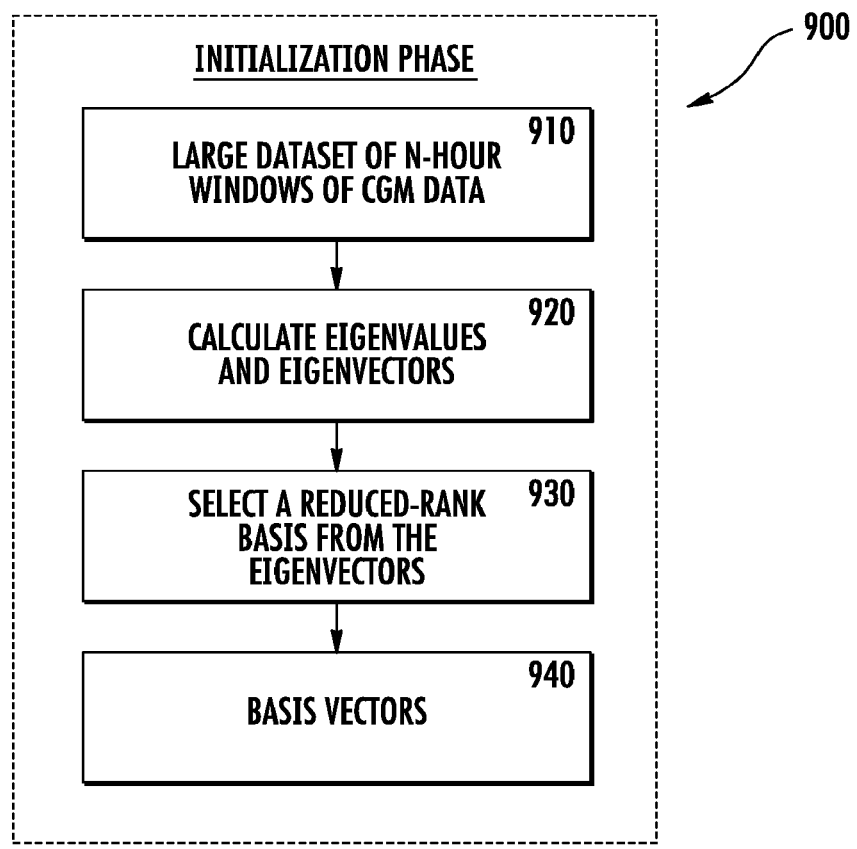
FIG. 9 depicts a flowchart of an initialization algorithm process for compressing data.

FIG. 9 depicts the initialization algorithm 900, which is the process used to find a transformation matrix to convert raw data vectors into compressed reduced-rank vectors. The initiation algorithm may occur one time to find the transformation matrix, and then the transformation matrix may be hard-coded into the pattern-matching algorithm 200, 800 running on the device 105 or patient monitoring system 100. Alternatively, the transformation matrix may be a separate compression algorithm from the pattern-matching algorithm 200, 800. The initiation algorithm may be run on a device separate from the device or system running the pattern-matching algorithm. By way of example only, the initiation algorithm may be run on a PC or other kind of computer.

As depicted, Block 910 represents the step of collecting a large representative sample of time window data sets of a desired length, N (length of a time window data set). The time window data sets may be from a single patient or more than one patient. The data, X, may be from diabetic patients in free-living conditions and may represent a broad range of patient behaviors and results so that it may be representative of a population of diabetic patients. The data, X, may be data from a previous study or may generally come from any large source of glucose measurement data. The data, X, may be centered and normalized, $\hat{X}$, to have a mean of zero and standard deviation of one, and thus may be expressed according to Equation (1) as follows:

$$\hat{X} = \frac{(X - \bar{x})}{\sigma_x}, \tag{1}$$

where X is the M×N matrix of K time window data sets each of length N, $\bar{x}$ is the mean time window data set vector over all K time window data sets, and $\sigma_x$ is the standard deviation time window data set vector over all K time window data sets, K is the length of the compressed reduced-rank vector, and M is the number of sample time window data sets for the initialization algorithm. Data from the time window may be augmented with one or more data tags as discussed above.

Block 920 represents the step of Eigen-decomposition, where the Eigen values and Eigen vectors for the matrix $\hat{X}^T\hat{X}$ is determined, which may be expressed according to Equations (2) and (3) as follows:

$$\lambda = \text{eigenvalues}(\hat{X}^T\hat{X}) \quad (2),$$

$$V = \text{eigenvectors}(\hat{X}^T\hat{X}) \quad (3).$$

The eigenvectors may be used as the new basis vectors with only the first K vectors, where K is the length of the compressed reduced-rank vector, being used in order to compress the data. The value of K is determined by sorting the Eigen values from largest to smallest, and then calculating the cumulative sum for the sorted list of Eigen values. The Eigen value may be used to show the amount of information explained by its corresponding Eigen vector. The Eigen vectors associated with the smallest Eigen values are removed to compress the data.

Block 930 represents the step of selecting a reduced-rank basis from the Eigen vectors. K may be selected to balance between compressing the data (for algorithm efficiency purposes) and retaining relevant information (level of detail needed in the data). Block 940 represents the step of compressing data into reduced-rank basis vectors. The first K Eigen vectors are used to create a transformation matrix, B, which converts time window data sets to the reduce-rank basis. A vector is compressed according to Equations (4)-(6) as follows:

$$B = [v_1, v_2, \ldots v_K], \quad (4)$$

$$\bar{x}_t = \frac{(x_t - \bar{x})}{\sigma_x}, \quad (5)$$

$$a_t = B^T \hat{x}_t, \quad (6)$$

where vector $a_t$ represents the reduced-rank version of $x_t$, $x_t$ is the time window data set of length N starting at time t, $B^T$ is the transformation matrix consisting of first K Eigen vectors $[v_1, v_2, \ldots v_K]$, and $v_i$ is the $i^{th}$ Eigen vector that corresponds to $\lambda_i$. The reduced rank vector $a_t$ can be converted back to the original space $\tilde{x}_t$ by multiplying by B, which may be expressed according to Equation (7) as follows:

$$\tilde{x}_t = B a_t \quad (7).$$

Data compression may provide, and not limited thereto, the following two noted benefits: it significantly reduces the size of the data for making comparisons, and functions as a filter for removing noise from the signal. Thus, the compression algorithm may match time window data sets with a similar underlying signal rather than matching noise patterns.

Algorithm Initiation Example

Figure 10:
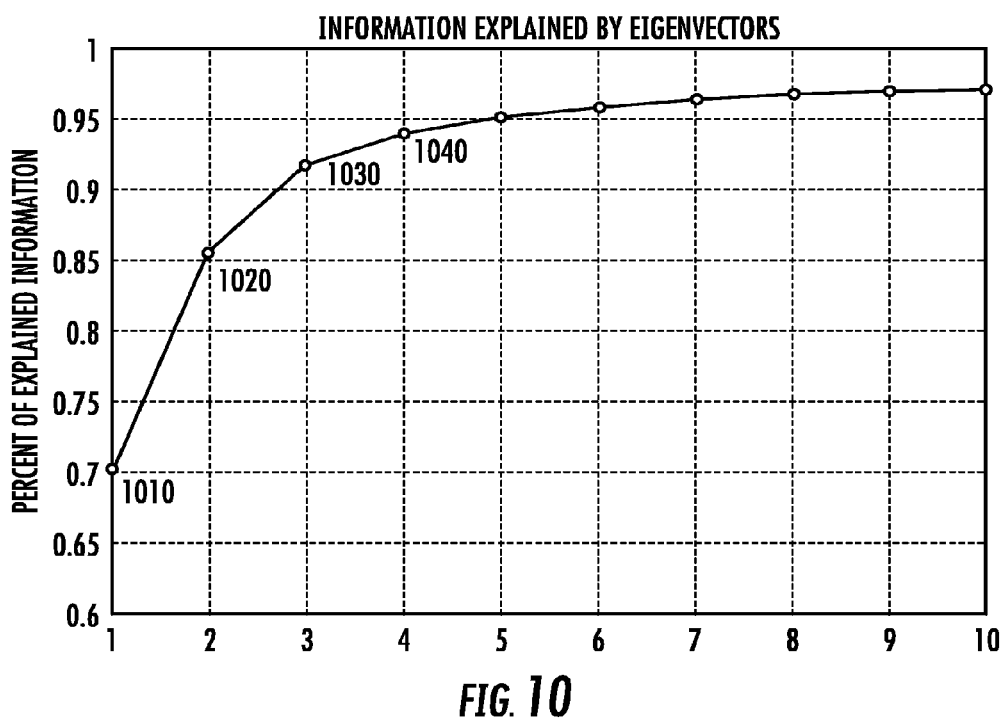
FIG. 10 depicts an exemplary cumulative sum chart of the largest Eigen values.

In some of the experiments performed, the length of each time window data/data segment set was four hours. Glucose concentration was measured each minute so each window contained a vector of 240 glucose measurement values. In other experiments performed, the length of each time window data set was two hours. Of course, other time window lengths may be used to collect glucose measurements. In step 1, where a large sample of time window data sets were collected, the length N of each time window data set was 240 minutes, as noted above, and over 100,000 time window data sets were used. The data was centered, normalized, and an Eigen decomposition was performed. The cumulative sum of the Eigen values from the Eigen decomposition was calculated. FIG. 10 depicts an exemplary plot of the cumulative sum of the largest Eigen values divided by the total sum of the Eigen values. The Eigen value may be used to show the amount of information explained by its corresponding Eigen vector. Thus, as shown in the plot on FIG. 10, compressing the time window data sets using the first Eigen vector 1010 would retain about 70% of the original data. Using two Eigen vectors 1020 would retain about 85% of the original data. Using three Eigen vectors 1030 would retain about 91% of the original data. Using four Eigen vectors 1040 would retain about 94% of the original data, and so on. In this example, K was selected to be four.

Figure 11:
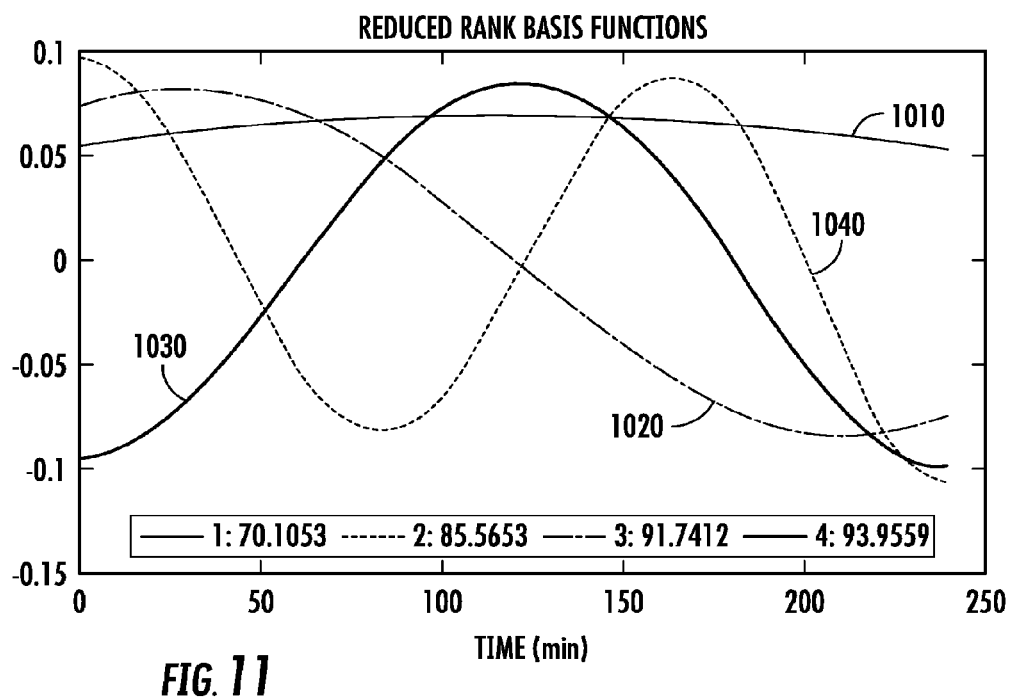
FIG. 11 depicts an exemplary plot of four Eigen vectors.

FIG. 11 depicts a plot of the first four Eigen vectors (1010, 1020, 1030, 1040) calculated using the data from this example, which shows the compressed vectors to be orthogonal. Each vector captures an important type of dynamic found in the raw data. The first Eigen vector 1010 is approximately the mean value of the raw data vector. The second Eigen vector 1020 measures the trend. The third Eigen vector 1030 captures peaks. The fourth Eigen vector 1040 responds to higher frequency components.

Figure 12:
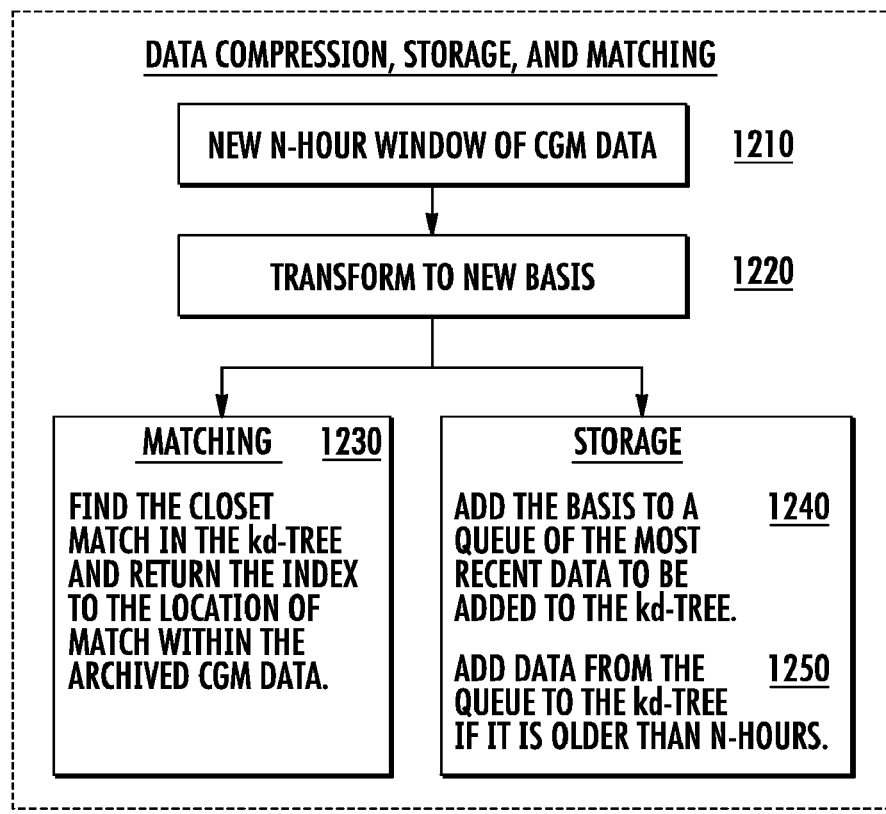
FIG. 12 depicts a flowchart of the match and storage phase of the pattern matching process of FIG. 7.

Referring back to FIG. 7, once the raw data has been compressed, the compressed data may be either pattern-matched by the processor 120 or 185, as represented by block 240, or stored in the database 130 (or alternatively, in memory 135) by the processor 120 or 185, as represented by block 235, both of which are further explained in FIG. 12. Block 245 represents the end of the algorithm.

Referring to FIG. 8, once the raw data has been compressed, the compressed data may be either pattern-matched by the processor 120 or 185, as represented by blocks 830, 835 and 840, or stored in the database 130 (or alternatively, in memory 135) by the processor 120 or 185, both of which are further explained in FIG. 12. Block 870 represents the end of the algorithm.

FIG. 8 also depicts blocks 845, 850, 855, 860, and 865, which generally represent the input and storage of a reference pattern and associated alert to be used during real-time pattern matching. Block 845 represents the input of a reference pattern and/or associated alert into input device 110 using user interface 145.

The reference pattern can be any data set of interest, e.g., historical data (previous day(s), week(s), month(s), year(s), etc.) of the patient 102. The data set can be provided from the input device 110, the database 130, the memory 135, the user interface 145, and/or from any another external source of patient data that the device 105 may communicate with via the data interface 115. It is to be appreciated that as such the reference pattern can be generated from any of the data available to the device 105, and by any method performed by the processor 120, the input device 110 (if provided with processing means), or an external device (s) operating on the data (and provided to the device via the data interface 115), in which to provide a pattern of interest, such as e.g., a glucose curve. Exemplary methods for generating a glucose curve may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The reference pattern can also be generated from data resulting from a query inputted via the user interface 145 and run by the processor 120 on stored data provided in database 130, memory 135 and/or in other external sources that were queried by the processor 120 via data interface 115. The reference pattern may also include any relevant data tags or multi-analyte data, and the generated and/or received reference pattern may be stored in the database 130 and/or memory 135 until needed by the processor 120 for a pattern matching process discussed hereafter in a later section.

The alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert. The alert may be displayed on display 140 of device 105.

In one example, the reference pattern and alert can be used to alert the patient to take specific actions whenever a particular event occurs. For example, the reference pattern can be a post-prandial event, hypoglycemic event, exercise, meals, etc. or any other problematic pattern that has occurred in the patient's past physiological data. Thus, when the event is detected again on a real-time basis, the patient monitoring system 100 will alert the patient to that fact.

Similar to block 825, block 850 represents the processing of the reference pattern to normalize and center the data by the processor to a scale where the distribution of glucose and/or physiological measurements has a mean of zero and standard deviation of one, Block 855 represents the compression of the reference pattern to a reduced-rank basis performed by the processor 120. The processor 120 or 185 may compress the reference pattern and store it for real-time comparison. Block 860 represents the storage of the compressed reference pattern and block 865 represents the storage of the alert in database 130 in a queue or in processor 120 or 185.

Block 830 represents the pattern matching steps which calculate the distance metric between the reference pattern and a real-time (or most current) time window data set. The pattern matching method is further described below in more detail. Block 835 represents the step of determining whether the distance metric is less than a certain value $\epsilon$ which may be set by the user. If the distance metric is less than $\epsilon$, then the alert is activated as shown in block 840. If the distance metric is greater than $\epsilon$, then no alert is activated and the algorithm repeats the process for the next current time window data set. Block 870 represents the end of the pattern-matching algorithm 800.

The pattern-matching algorithm 200, 800 may run on any suitable computing device or system, such as device 105, patient monitoring system 100, or provided on a non-transitory computer-readable medium that stores the pattern-matching algorithm 200, 800 in the form of a program providing instructions that when executed by a processor, such as processor 120 or 185, causes the processor to perform the above described acts of blocks 202-245 of FIG. 7 and blocks 802-870 of FIG. 8. The pattern-matching algorithm 200, 800 may be used for efficiently finding the best match or matches to a reference pattern. FIG. 12 further describes the pattern-matching (block 235 of FIG. 7 and blocks 830, 835 and 840 of FIG. 8) and storage phase of the algorithm (block 240 of FIG. 7). Prior to pattern-matching 1230, the current time window data set 1210 is centered and normalized, then transformed into the reduced-rank space 1220 using the transformation matrix, B, that was calculated previously using the initiation algorithm, and which may be expressed according to Equations (8)-(9) as follows:

$$\hat{x}_t = \frac{(x_t - \bar{x})}{\sigma_x}, \qquad (8)$$

$$a_t = B^T \hat{x}_t. \qquad (9)$$

The closest match or matches may be determined using a distance metric, $j_i$. In one example, the distance metric is the Euclidean distance where the difference in position of two vectors is calculated within the reduced-rank space 1220. Thus, $a_t$ is found by calculating the value that minimizes Equation (10) as follows:

$$j_i = \sqrt{(a_i - a_t)^T (a_i - a_t)} \qquad (10),$$

where $a_i$ is the reduced-rank vector of a stored time window data set selected as a potential match, $a_t$ is the reduced-rank reference vector, and T is the transpose function. For real-time pattern matching shown in FIG. 8, the alert is displayed if the value of the distance metric, $j_i$, is less than a threshold value, $\epsilon$. The value for epsilon depends on the distance metric selected, noise penalty, length of time window, etc. In one example, $\epsilon$ is selected to, but can be substantially close to zero. In a general case, $\epsilon$ may be selected using common statistical tests, for e.g., regression analysis, so that the probability that the matches are measurements of the same physiological data is at least 0.95 or in a more stringent case 0.98.

$$j_i \leq \epsilon \qquad (11),$$

In another example, the distance metric is the Mahalanobis distance, which also takes into account the correlations of the data set.

$$j_i = \sqrt{(a_i - a_t)^T \Sigma^{-1} (a_i - a_t)} \qquad (12),$$

where $\Sigma^{-1}$ is the inverse of the covariance matrix. Of course, other distance metrics may be used to perform pattern matching and will be apparent to those of ordinary skill in the art in view of the teachings herein.

A modified Euclidean distance metric may be used, where the Euclidean distance is modified with an error penalty function to penalize raw data that is too distorted. In one example, the distortion over a raw data window may be estimated by calculating the sum of the absolute error between the compressed data and its raw data, which may be expressed according to Equation (13) as follows:

$$e_i = \Sigma |g_i - \tilde{g}_i|, \text{ where } \tilde{g}_i = B a_i \qquad (13),$$

where $e_i$ is the sum of the absolute error, $g_i$ is the absolute error of the raw data, and $\tilde{g}_i$ is the absolute error of the compressed data that may be determined to find the closest match or matches that are both close and have less distortion. The closest match or matches may be determined using the Euclidean distance within the reduced-rank space, for example, by calculating the value that minimizes Equation (14) as follows:

$$j_i = \sqrt{(a_i - a_t)^T (a_i - a_t)} + \mu e_i \qquad (14)$$

where $\mu$ is a parameter used to tune the balance between minimizing the distance and error. This distance metric will tend to find patterns that are both similar and with lower distortion. The value of $j_i$ can be used to evaluate the quality of the match. For example, if $j_i$ is less than some threshold then the match could be qualitatively described as "excellent," "good," or "poor." The distance metric may include components representing the difference between tags associated with the data.

$$e_{tag} = f(k_p, k_t) \qquad (15).$$

In operation, when the pattern-matching algorithm 200 is executed by a processor, e.g., processor 120 or 185, it can cause the processor to further perform the pattern match by determine the distance metric between the nearest neighbor and the reference pattern. In another example, when the pattern-matching algorithm 200 is executed by the processor 120 or 185, it can cause the processor to further perform the pattern match by determine the distance metric between the nearest d neighbors and the reference pattern. In another example, when the pattern match algorithm is executed by a processor, e.g., processor 120 or 185, it can cause the processor to further perform the pattern match by determine the distance metric between at least one data point within some range r of the reference pattern, where r is the desired distance from the reference pattern. Pattern-matching algorithm 800, when executed by a processor 120 or 185, it can cause the processor to pattern-match using the most recent or current time window data set and the reference pattern. When the most recent or current time window data set matches the reference pattern, the device 105 triggers an alert, which can include the display of an alert message containing therapy information.

The pattern-matching algorithm 200, 800 may be run on, for example, a continuous glucose monitor system or other patient monitoring systems as described above. The pattern-matching algorithm 200, 800 may also be run on other exemplary continuous glucose monitors manufactured by, for example, Medtronic, DexCom, and Abbott Diabetes Care or any other system that may be used to display and/or analyze raw data from a physiological sensor, and/or reference patterns from actual or generated data, for patterns.

In one example, a patient monitoring system runs a pattern matching algorithm. The patient monitoring system comprises an input device which receives a biological sample and acquires a plurality of physiological measurements of a patient within a time window thereby generating at least one time window data set, a memory storing a pattern matching algorithm, a database to store the at least one time window data set, and a processor in communication with said input device to receive said generated at least one time window data set and in communication with the memory in order to execute the pattern matching algorithm. When the pattern matching algorithm is executed by the processor, it causes the processor to compress the at least one time window data set into a reduced-rank space and perform a pattern match between a reference pattern and the stored at least one time window data set using a distance metric. The memory may further store a data pre-processing algorithm. The data pre-processing program, when executed by said processor, may cause said processor to normalize and center the at least one time window data set to a scale where the distribution of the plurality of physiological measurements has a mean of zero and a standard deviation of one.

The generated at least one time window data set may be compressed into a reduced-rank space using a transformation matrix. The transformation matrix may be determined by an initialization algorithm, which when executed by the processor, causes the processor to perform an Eigen-decomposition on a large, representative physiological measurement dataset to determine $\lambda$ eigenvalues and V eigenvectors, calculate the cumulative sum of the eigenvalues, and select a subset K of the largest Eigen vectors. By way of example only, K can be six or less. In another example, K can be five or less. In another example, K can be four or less. By way of example only, K may also be preselected to retain up to about 90% of the original data from the at least one time window data set. In another example, K may be preselected to retain up to about 95% of the original data from the at least one time window data set. In another example, K may be preselected to retain up to about 98% of the original data from the at least one time window data set.

When the pattern matching algorithm is executed by said processor, it may cause the processor to pattern match by determining the distance metric within the reduced-rank space. It may also cause the processor to pattern match by determining the closest match that calculates the value that minimizes the distance metric within the reduced-rank space. The pattern matching algorithm, when executed by said processor, may further cause the processor to determine the absolute error of a pattern match using the distance metric within the reduced-rank space or of the closest match that minimizes the distance metric within the reduced-rank space. The processor may perform the pattern match using a Kd-tree search or a naïve exhaustive search.

The patient monitoring system may further comprise a database and one or more storage algorithms. When the one or more storage algorithms are executed by said processor, it may cause the processor to store a compressed dataset in a Kd-tree structure in the database. It may also cause the processor to add the compressed dataset to a queue, and then add the compressed dataset from the queue to the Kd-tree structure. By way of example only, data sets may be stored in the database at a regular interval, based on an event, based on a data tag, based on the pattern of the data, or when requested by the user.

In another example, a patient monitoring comprising a sensor and a processor may use the pattern-matching algorithm for processing at least one time window data set. In operation, the patient monitoring automatically receives via the sensor a biological sample into the patient monitoring, acquires a plurality of physiological measurements automatically generates at least one time window data set, and automatically has the processor process the generated at least one time window data set to normalize and center the at least one time window data set to a scale where the distribution of physiological measurements has a mean of zero and a standard deviation of one, compress the normalized at least one time window data set into a reduced-rank space, and perform a pattern match between a reference pattern and the compressed at least one time window data set using a distance metric within a reduced-rank space.

During the pattern match, the processor may automatically find the closest match by calculating the smallest distance metric value between the reference pattern and one of the stored at least one time window data set (i.e., potential match) to find the closest match within the reduced-rank space. This may be done by performing a Kd-tree search or by performing a naïve exhaustive search. The processor may also automatically find the absolute error of the pattern match or closest match.

The processor may automatically compress the generated or normalized dataset into a reduced-rank space by performing an eigen-decomposition via decomposing an $X^T X$ matrix into λ eigenvalues and V eigenvectors. Then the processor may automatically calculate the cumulative sum of the eigenvalues, determine the corresponding eigenvector for each eigenvector, and select a subset of eigenvectors by balancing between data compression and preservation of relevant information. The processor may automatically apply an orthogonal transform matrix to said subset of eigenvectors to provide a compressed reduced-rank vector. The processor may also automatically store the compressed dataset in a Kd-tree.

In another example, a non-transitory computer-readable medium may store the pattern matching algorithm in the form of a program. When the program is executed by a processor, it causes the processor to perform at least a pattern match of a reference pattern to a stored data time window data set collected via a patient monitoring system using a distance metric. The program may cause the processor to perform the pattern match by finding the nearest neighbor to the reference pattern. In another example, the program causes the processor to perform the pattern match by finding the nearest d neighbors, where d is the number of neighbors of interest. In a further example, the program causes the processor to perform the pattern match by finding at least one data point within some range r of the reference pattern, where r is the desired distance from the reference pattern. The program may cause the processor to further perform the pattern match by determine the absolute error between the nearest neighbor and the reference pattern, between the nearest d neighbors and the reference pattern, and/or between the at least one data point within some range r of the reference pattern, where r is the desired distance from the reference pattern.

As noted above, when running a pattern matching algorithm, the reference pattern can be the most recent at least one time window data set (except for where a real-time pattern matching algorithm is running) and/or can be any other pattern of interest, e.g., a diabetes patient's past data, another source of glucose data, a generated glucose curve, etc. Exemplary methods for generating a glucose curve may include: drawing a glucose curve using, for example, a mouse, a keyboard, a touch screen, etc., selecting a glucose curve that represents a common behavior or condition (e.g., falling blood glucose during exercise, rise of blood glucose after a meal, etc.), etc. The glucose curve need not be selected from actual glucose data measurements, but can be selected from actual glucose measurement data. The reference pattern may also include relevant data tags.

The pattern matching algorithm can be used in a variety of ways. For example, pattern matching can be performed to identify problematic meals. At times, diabetic patients are face with the challenge of controlling post-prandial (i.e., after a meal) hyperglycemic excursions. Diabetic patients can monitor their post-prandial glucose behavior by glucose testing at a distinct time after a prandial event. This, however, may neglect the dynamics of the glucose excursion, that is, the change in glucose or other relevant data (e.g., carbohydrate intake, other meal information, insulin levels, etc.) after a meal. The pattern matching algorithm may be used by a diabetic patient or health care provider to draw quickly a reference pattern of the hyperglycemic post-prandial event that corresponds to the dynamics of the meals a patient has consumed. Finding patterns in the patient system that are similar to the reference pattern may allow for identification of problematic meal events. A health care provider or diabetic patient may correct these events in the future by more accurately estimating the carbohydrate content or modifying treatment appropriately. The pattern matching algorithm may also be used to identify multiple instances where hyperglycemia was most severe and determine patterns that may have caused these deviations. The pattern matching may be used to identify similar meals. A search of past data may be made for similar glucose patterns and/or behavioral patterns to assist a diabetic patient to recollect past decisions and outcomes. In operation, a user may draw or select a pattern, and the system calculates the percentage of time that a diabetic patient's closest match data is similar to the reference pattern within certain boundaries.

In another example, pattern matching can be performed to identify hypoglycemic events. Diabetic patients are also sometimes faced with undetected nocturnal hypoglycemic episodes. Undetected hypoglycemic episodes are possible on account of both meal-influenced glucose-insulin dynamics and physical activity. A reference pattern may be used by a user to identify periods where the patient experienced hypoglycemia to analyze these episodes to provide a framework for identifying hypoglycemia causes and providing solutions. For example, the combination of closest match patterns and meal, insulin, and physical activity information may serve as a useful tool in analyzing patient hypoglycemic behavior. It may also indicate strategies to avoid hypoglycemia. In operation, a user may draw or select a pattern, and the system calculates the percentage of time that the diabetic patient's closest match data is similar to the reference pattern within certain boundaries.

In another example, pattern matching can be performed to estimate proactively bolus or meal intake. A reference pattern and meal information may be used by a user to search through a meal database and observe past glycemic behavior. The user may then analyze post-prandial behavior based on the past event, and make insulin bolus changes to avoid a post-prandial hyperglycemic excursion. Similarly, a user can use past physical activity, insulin and meal information to correct for impending hypoglycemic episodes before exercising or other physical activity.

In another example, pattern matching may be used in a real-time patient monitoring system (running the real-time pattern matching algorithm) to notify a patient if a most recent or current time window data set is substantially similar to a reference pattern. The reference pattern is input into the device along with an alert that will display when the monitoring system identifies a most recent or current time window data set that is substantially similar to the reference pattern. When the most recent or current time window data set matches the reference pattern, an alert will be triggered. The reference pattern can be any problematic pattern in the patient's physiological data (e.g., post-prandial behavior, hypoglycemic events, hyperglycemic events, exercise, etc.)

Referring to FIG. 12, during the storage phase, data that is available and compressed may be added to a queue 1240. The queue contains the most recent compressed vectors waiting to be added to the kd-tree. The compressed vectors are moved from the queue to the kd-tree when they are older than N, where N is the length of the current time window 1250. Thus, the compressed vectors are moved to the kd-tree when they are no longer overlapping with the current time window. The time windows are represented in the kd-tree by their k-dimensional compressed vector and a time parameter that links the compressed vector to a location in the saved raw data.

Pattern Match Examples

Exemplary pattern match results were generated by finding the closest match in a database containing 138,489 stored four-hour data windows compressed into 4-dimensional vectors. For each time window, the closest match was found in the reduced-rank space. The searches were performed using a naïve exhaustive search and the efficient kd-tree search. Details of the exemplary pattern match results will be discussed in more detail below using FIGS. 13(a) and 13(b), 14(a) and 14(b), 15(a)-15(c), 16(a)-16(e) and 17.

Figure 13A:
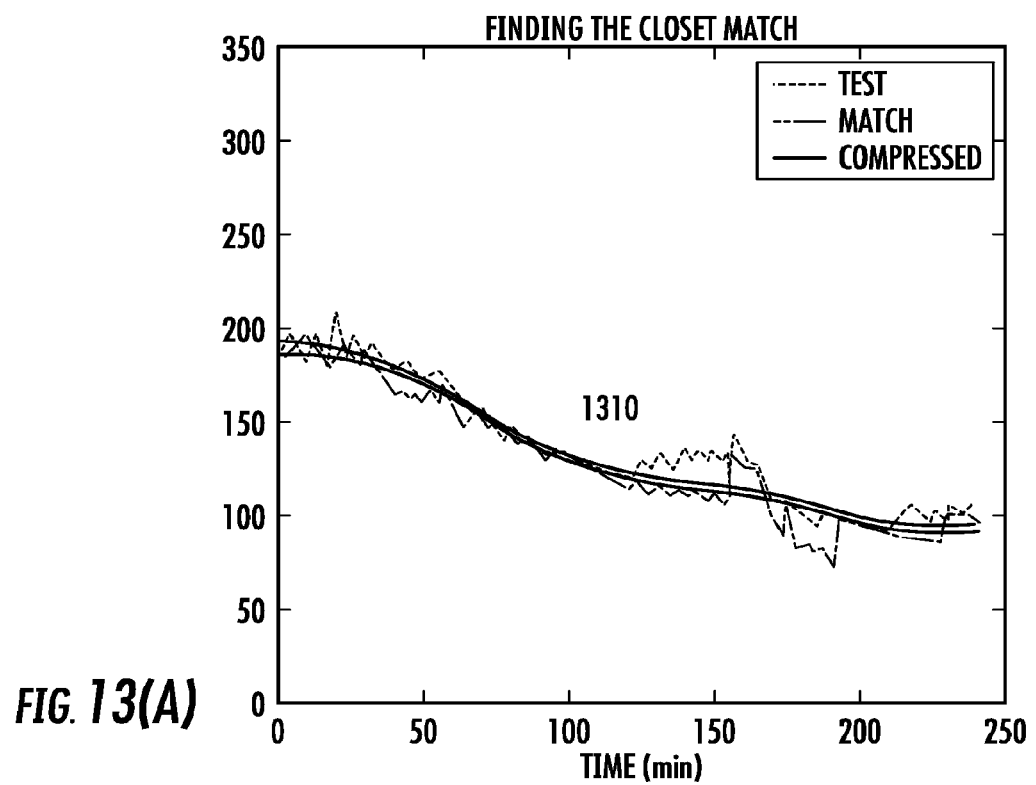
FIGS. 13(a) and 13(b) depict exemplary pattern match plots having a downward trend.
Figure 13B:
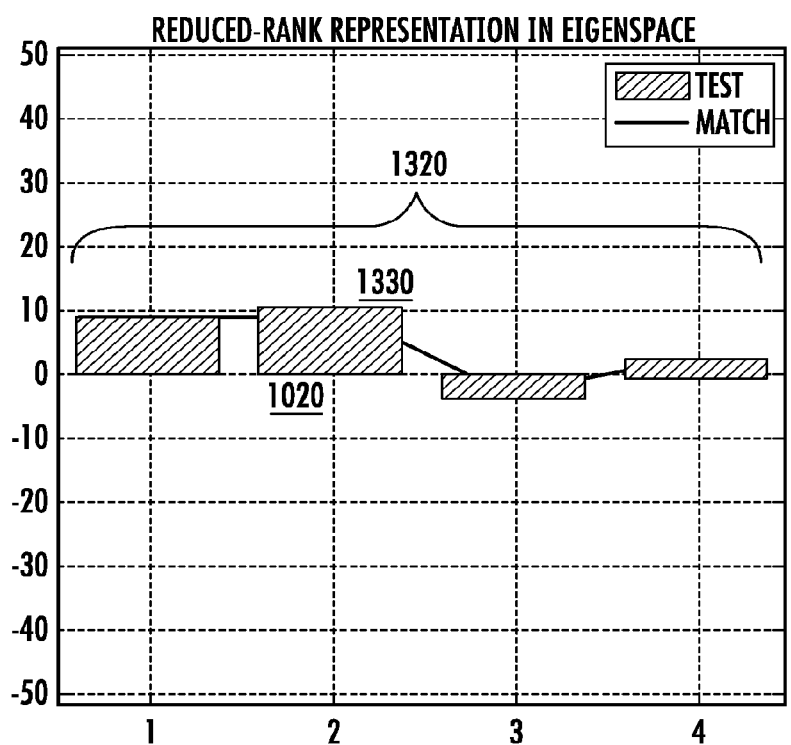
Figure 14A:
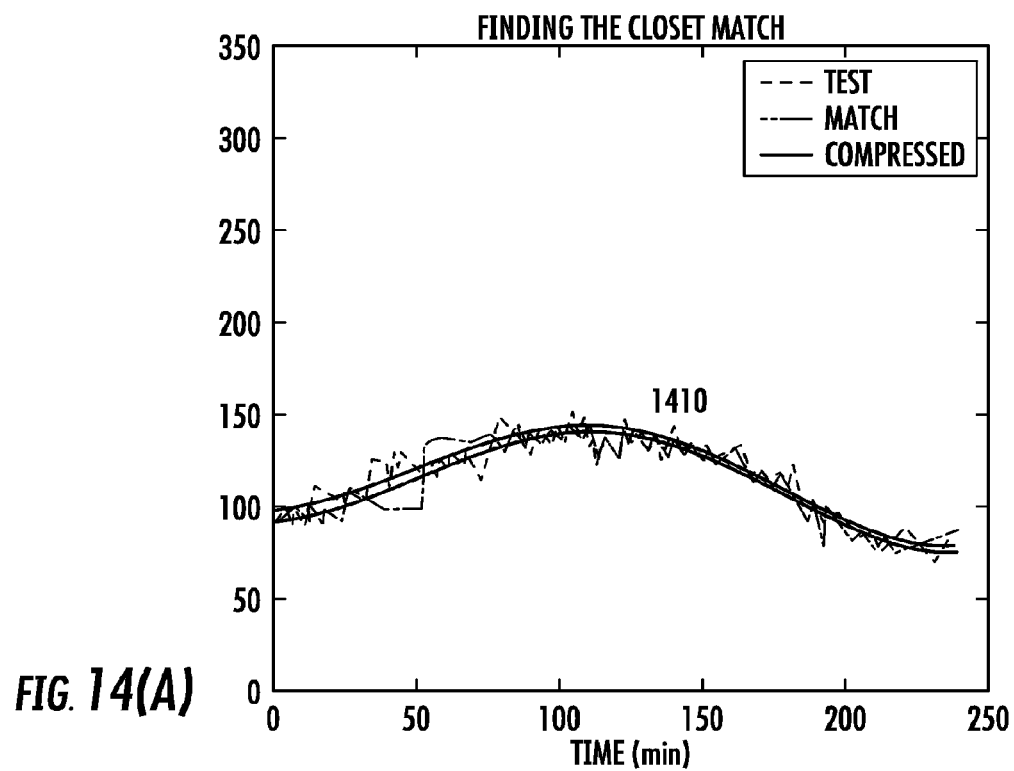
FIGS. 14(a) and 14(b) depict exemplary pattern match plots having a peak.
Figure 14B:
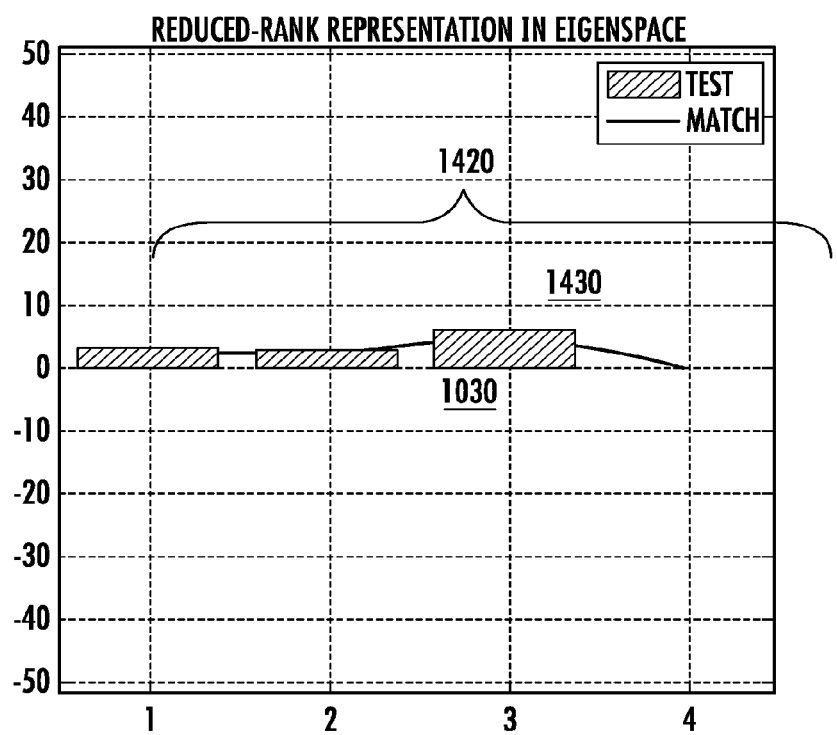

FIGS. 13(a), 13(b), 14(a) and 14(b) depict two results from an exemplary pattern-match search for the closest match. FIGS. 13(a) and 14(a) show exemplary plots (1310, 1410) of the time window raw data used for the pattern-match search, its compressed version, and the raw data of a match along with its compressed version. FIGS. 13(b) and 14(b) show exemplary plots of the value of the compressed vectors with the time window data plotted as bars (1330, 1430) and the match as a line (1320, 1420). The exemplary plots of FIGS. 13(a) and 13(b) show a downward trend so the second Eigen vector 1020 contains the strongest response. The exemplary plots of FIGS. 14(a) and 14(b) show a peak so the third Eigen vector 1030 contains the strongest response. The ability to interpret the values in the reduced-rank space could be used for other algorithms, such as hypoglycemia prediction, meal pattern classification, and noise-filtering.

Figure 15A:
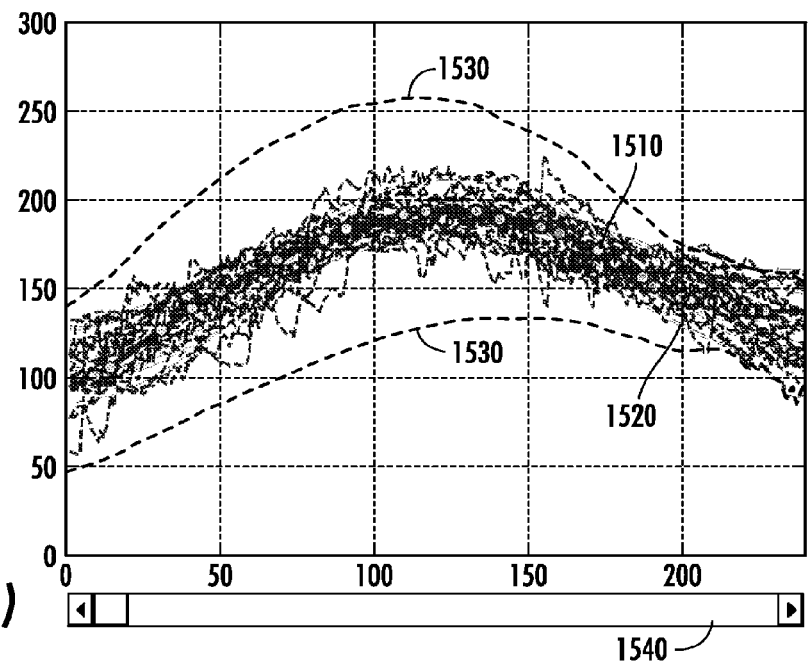
FIGS. 15(a)-15(c) depict exemplary displays of pattern match plots over a 4 hour time period.

FIG. 15(a) depicts an exemplary display of a reference pattern plot of blood glucose concentration over time. In this example, a four hour reference pattern 1510 (shown as a line with circle points) was drawn and the pattern matching algorithm returned the reduced rank vectors of the top 20 matches 1520 shown as smooth lines. The noisy lines are the top 20 matches shown as raw data vectors. The top 20 matches 1520 were determined using Euclidean distance in the reduced-rank space and the sum of absolute error between the potential match's raw data vector and its reduced-rank vector. As depicted, the plot contains the reference pattern 1510 and all 20 matches 1520. Alternatively, the plot may contain the reference pattern and one or more matches. The plot may also contain error boundaries 1530 that range from about +/−15% to +/−50%. The error boundaries 1530 may be useful for showing a visual comparison. Also, shown is a scroll bar 1540 at the bottom of the screen that may be used to scroll through and/or select a specific match. The scroll bar 1540 may be a touch sensitive display, whereby the scroll bar on the screen is touched with a finger and then moving the finger in a desired direction on the screen. The arrows to the left and right of scroll bar 1540 may be touched with a finger on the screen to scroll through and/or select a specific match. In addition, a mouse may also be used to scroll through using scroll bar 1540 or the left and right arrows. As a specific match is selected, the display changes to highlight the specific match. Matches that are not selected may be dimmed and placed in the background.

Figure 15B:
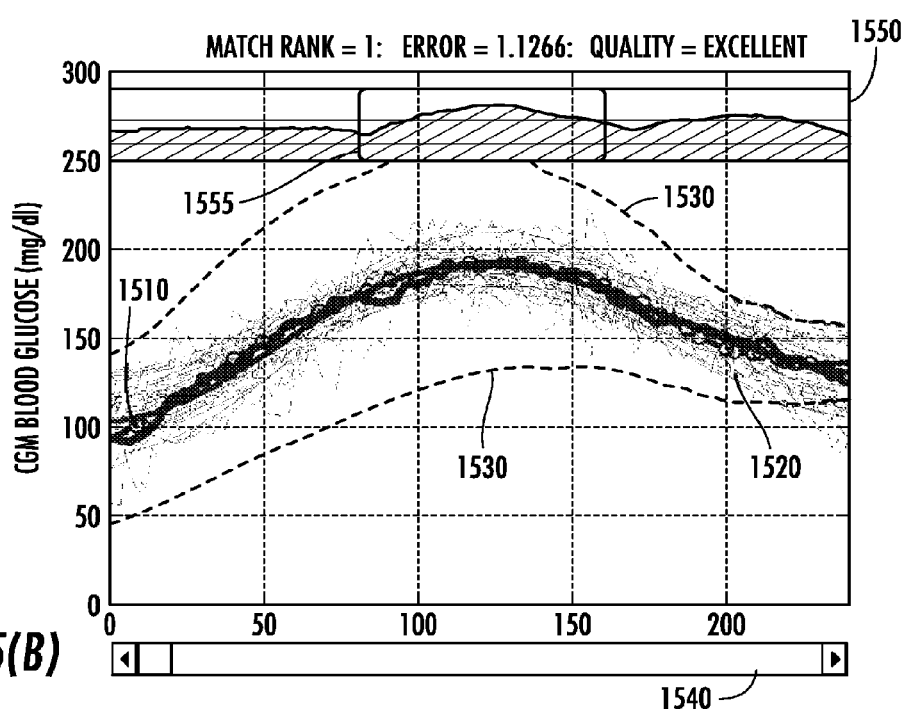

FIG. 15(b) depicts an exemplary display of a reference pattern plot of blood glucose concentration over time. Similar to FIG. 15(a), the plot contains the four hour reference pattern 1510 (shown as a line with circle points), reduced rank vectors of all 20 matches 1520 (shown as smooth lines), raw data vectors of all 20 matches (shown as noisy lines), error boundaries 1530 and scroll bar 1540. Also depicted are two highlighted lines showing the reduced rank vector of a particular match and the corresponding raw data vector (which is the noisy highlighted line) for the match. The display also includes a match rank, which ranks the matches in order from closest to Nth closest match, where N is the number of matches. In this particular example, the match rank can range from 1 to 20. FIG. 15(b) shows a match rank of 1 indicating that the highlighted match is the closest match to the reference pattern. The other matches are dimmed and placed in the background. Also depicted is a match error, which shows the absolute error between the match and the reference pattern. The quality assessment label is also depicted and is based on the match error numbers. A quality assessment label may comprise excellent, good, fair, poor, bad, awful, etc. or other label may be used to indicate the quality of a match. The display includes a timeline 1550 at the top of the graph, which depicts the matched section 1555 placed in a timeline that may provide context of the match.

Figure 15C:
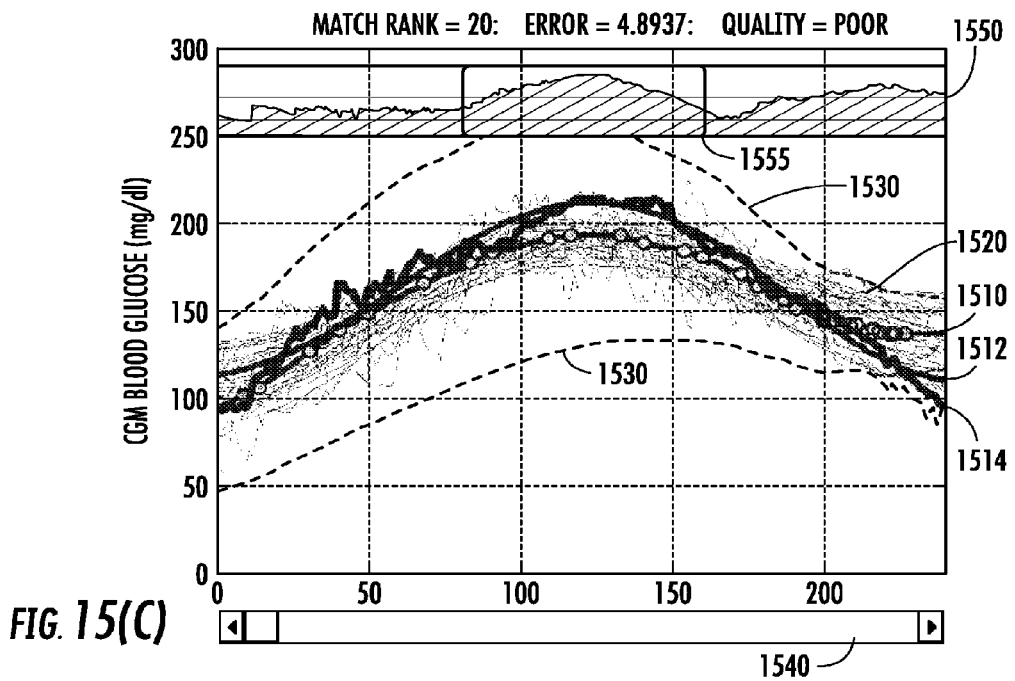

FIG. 15(c) depicts another exemplary display of a reference pattern plot of blood glucose concentration over time. Similar to FIGS. 15(a) and 15(b), the plot contains the four hour reference pattern 1510 (shown as a line with circle points), reduced rank vectors of all 20 matches 1520 (shown as smooth lines), raw data vectors of all 20 matches (shown as noisy lines), error boundaries 1530 and scroll bar 1540. Also depicted are two highlighted lines showing the reduced rank vector of a particular match 1512 and the corresponding raw data vector 1514 (which is the noisy highlighted line) for the match. FIG. 15(c) depicts a match rank of 20 indicating that the highlighted match is the 20th closest match to the reference pattern. The other matches are dimmed and placed in the background. Also depicted is the match error and quality assessment label. The display in this example shows a high match error and therefore, the quality assessment label is poor. The display also depicts a timeline 1550 at the top of the graph showing the matched section 1555.

Figure 16A:
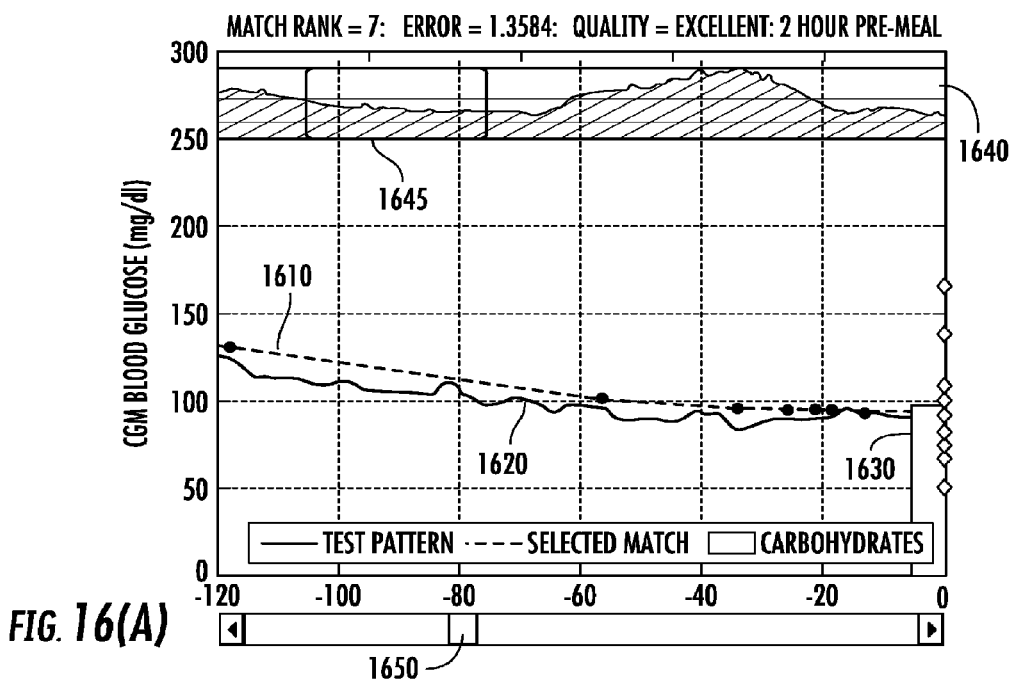
FIGS. 16(a)-16(e) depict exemplary displays of pattern match plots over a 2 hour time period.

FIG. 16(a) depicts an exemplary display of a reference pattern plot of blood glucose concentration over time and includes matching with a meal time tag. In this example, matches 1620 were determined for the two hours of data just prior to a meal in order to assist the user to evaluate possible outcomes for a meal based on past behaviors. Shown in FIG. 16(a) is the carbohydrates value for the meal. By way of example only, pattern matching may be done using a reference pattern 1610, a meal time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match. In this example, the actual outcome of the meal may be seen. Reference pattern 1610 was drawn and the pattern matching algorithm returned the top matches 1620. As depicted, the plot contains the reference pattern 1610 and the 7th best match 1620. Of course, the plot may contain the reference pattern and one or more matches. Also, shown is a scroll bar 1650 at the bottom of the screen that may be used to scroll through and/or select a specific match. The scroll bar 1650 may be a touch sensitive display, whereby the scroll bar on the screen is touched with a finger and then moving the finger in a desired direction on the screen. The arrows to the left and right of scroll bar 1650 may be touched with a finger on the screen to scroll through and/or select a specific match. In addition, a mouse may also be used to scroll through using scroll bar 1650 or the left and right arrows. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 16B:
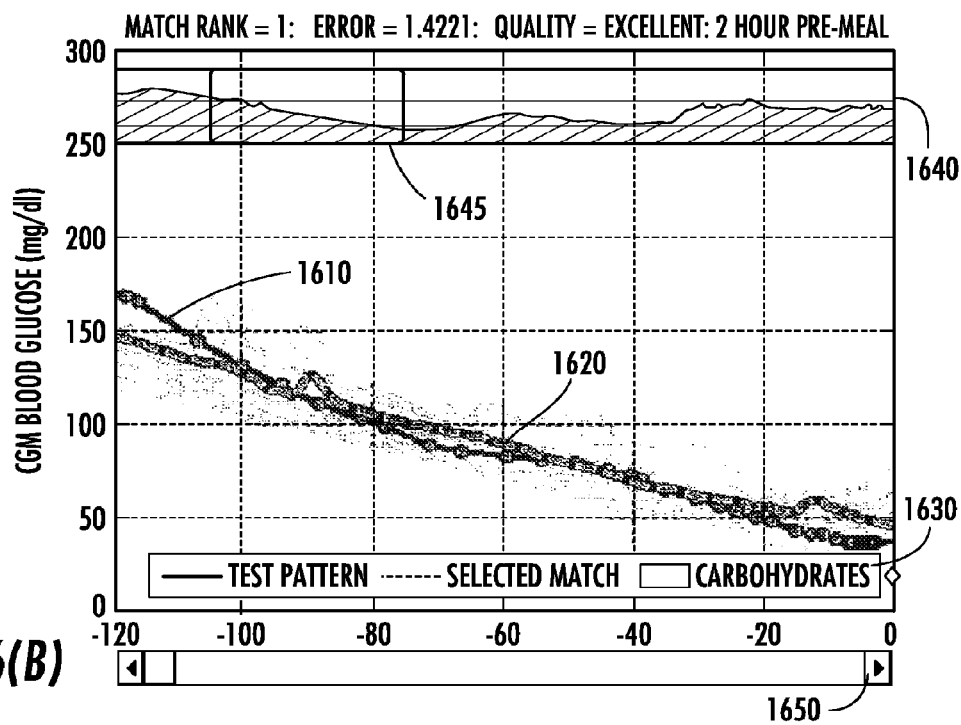

FIG. 16(b) depicts an exemplary display of a reference pattern plot of blood glucose concentration over time and includes matching with a meal time tag. In this example, the reference pattern 1610 is drawn to find instances of when a user may have been going into hypoglycemia and/or took carbohydrates to correct for the hypoglycemia. The display may be used to evaluate a patient's ability to correctly recover from hypoglycemia without overshooting into hyperglycemia. Matches 1620 were determined for two hours of data. The carbohydrates value (not shown) for the meal can be plotted. By way of example only, pattern matching may be done using a reference pattern 1610, meal time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match 1620. In this example, the actual outcome of the meal may be seen. Reference pattern 1610 was drawn and the pattern matching algorithm returned the top matches. As depicted, the plot contains the reference pattern 1610 and the best match 1620. Of course, the plot may contain the reference pattern 1610 and one or more matches 1620. Also, shown is a scroll bar 1650 at the bottom of the screen that may be used to scroll through and/or select a specific match 1620. The display also includes a match rank, which ranks the matches in order from closest to Nth closest match, where N is the number of matches. In this particular example, FIG. 16(b) shows a match rank of 1 indicating that the highlighted match is the closest match to the reference pattern. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 16C:
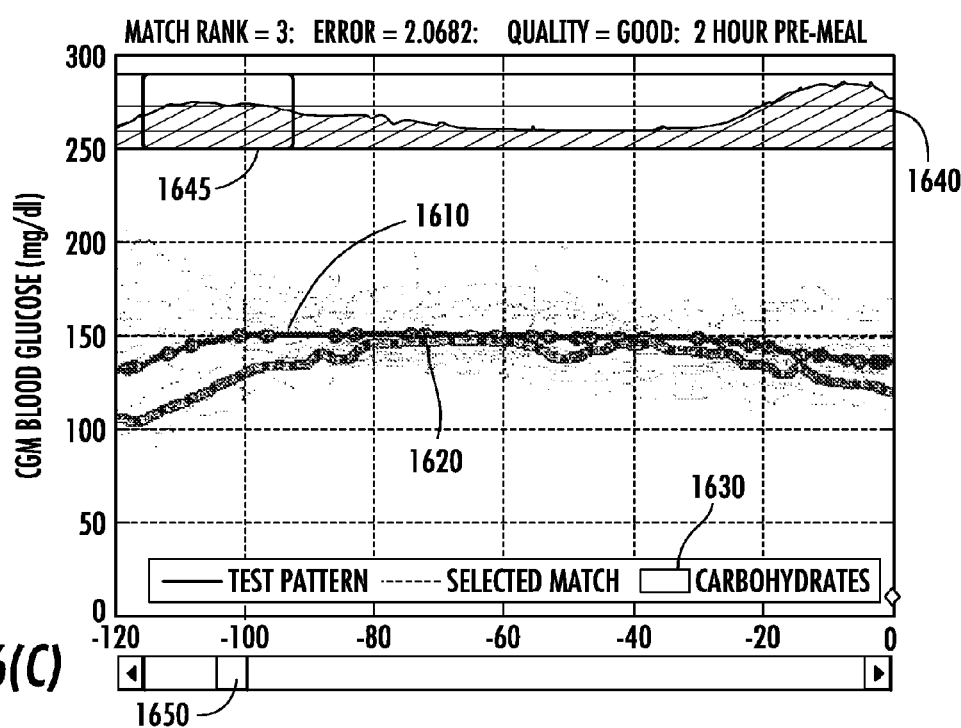

FIG. 16(c) depicts an exemplary display of a reference pattern plot of blood glucose concentration over time and includes matching with a sleep time tag. In this example, the reference pattern 1610 is selected for the two hour period prior to a subject going to sleep. The display may be used to evaluate the likelihood of nocturnal hypoglycemia based on the current state of the patient and their historical data. Matches 1620 were determined for two hours of data. The carbohydrates value (not shown) can be plotted. By way of example only, pattern matching may be done using a reference pattern 1610, sleep time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match 1620. Reference pattern 1610 was selected and the pattern matching algorithm returned the top matches. As depicted, the plot contains the reference pattern 1610 and a match 1620. Of course, the plot may contain the reference pattern 1610 and one or more matches 1620. Also, shown is a scroll bar 1650 at the bottom of the screen that may be used to scroll through and/or select a specific match 1620. The display also includes a match rank, which ranks the matches in order from closest to Nth closest match, where N is the number of matches. In this particular example, FIG. 16(b) shows a match rank of 3 indicating that the highlighted match is the third closest match to the reference pattern. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 16D:
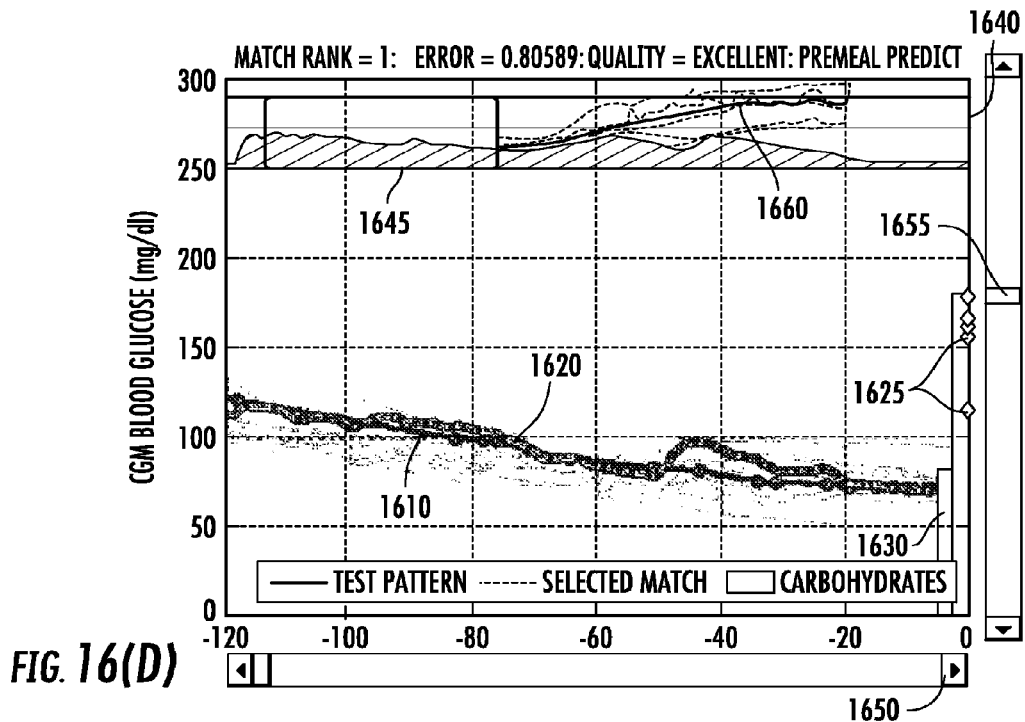
Figure 16E:
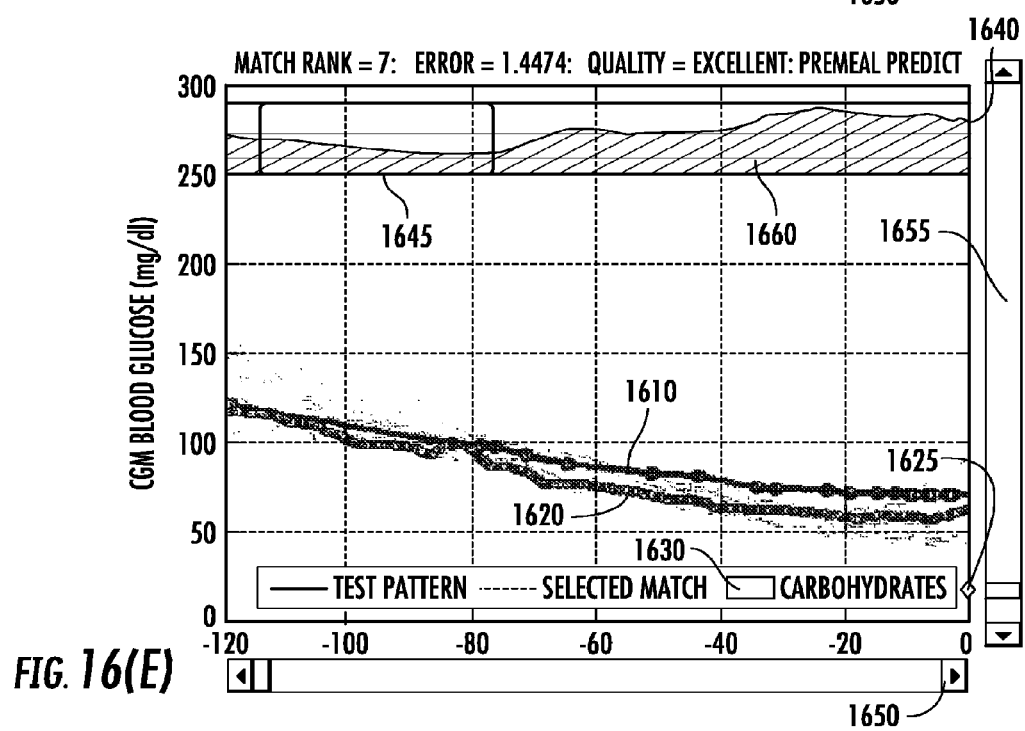

FIGS. 16(d) and 16(e) depict exemplary displays of a reference pattern plot of blood glucose concentration over time and includes matching using glucose levels, meal time tags, and carbohydrate values. Predictions of future glucose concentrations can be generated based on the matched data. The two figures depict a reference pattern 1610 with two different carbohydrate levels 1630 (shown only in FIG. 16(d)). The reference pattern 1610 and carbohydrate levels 1630 may be used to predict future blood glucose levels 1660, which are depicted in the timeline 1640. In this example, the reference pattern 1610 are selected for the two hour period prior to a meal. Reference pattern matches 1620 and carbohydrate matches 1625 were determined and plotted using the pattern matching algorithm. By way of example only, pattern matching may be done using a reference pattern 1610, glucose levels, meal time tags, and/or the current carbohydrate value 1630 that is being displayed. The displays shown include a timeline 1640 at the top of the reference pattern plot, which depicts the 2 hour matched section 1645 placed in a timeline with data shown on either side of matched section 1645 that may provide context of the match 1620. As mentioned above, timeline 1640 may also depict future blood glucose level predictions 1660. Also, shown is a horizontal scroll bar 1650 at the bottom of the screen that may be used to view the entire plot and/or scroll through matches. A vertical scroll bar 1655 may be used to scroll through and select or set the desired carbohydrate value 1630 to include in the reference pattern 1610. It may also be used to select a specific match 1620. The scroll bar 1655 may be a touch sensitive display, whereby the scroll bar on the screen is touched with a finger and then moving the finger in a desired direction on the screen. The arrows above and below scroll bar 1655 may be touched with a finger on the screen to scroll through and/or select a specific match. In addition, a mouse may also be used to scroll through using scroll bar 1655 or the up and down arrows. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 17:
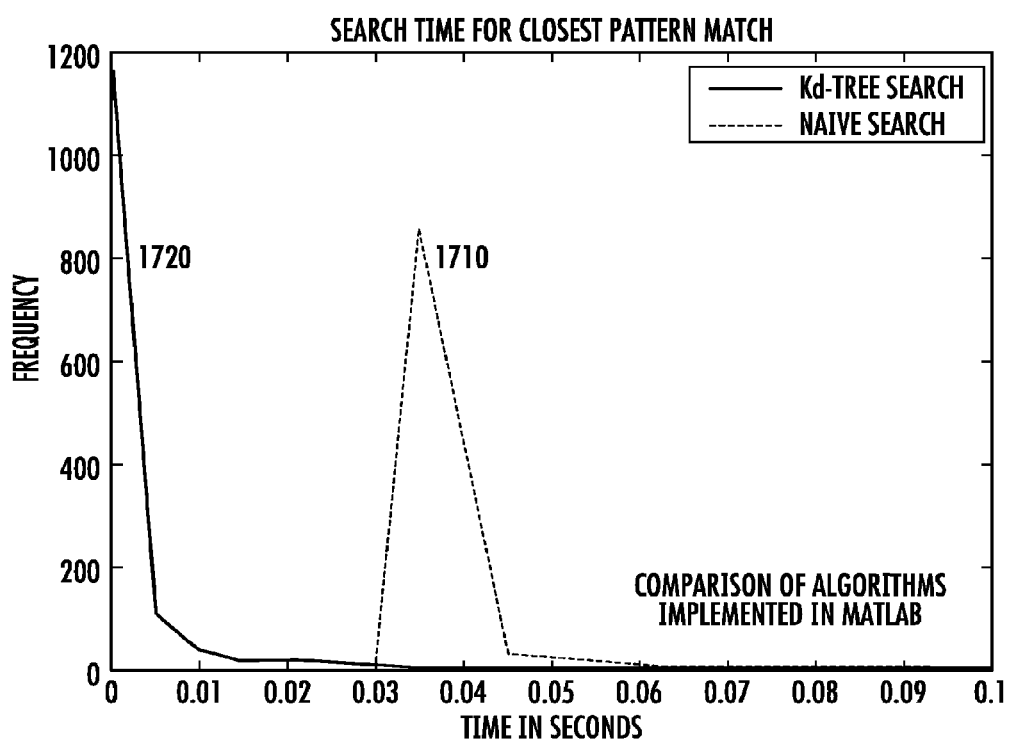
FIG. 17 depicts an exemplary plot of average search time in a pattern matching process.

FIG. 17 depicts an exemplary plot of the average search time for finding the closest match in the reduced-rank space when using two algorithms: a naïve exhaustive search 1710 and the kd-tree search 1720. Both algorithms may be used for searches and may be relatively efficient due to the compression algorithm; however, in this example, the kd-tree search 1720 significantly reduced the search time from an average of about 0.038 seconds to less than about 0.005 seconds.

Clustering

As indicated earlier, clustering has been reported in U.S. application Ser. No. 13/912,318, "A Method of Screening for Disorders of Glucose Metabolism," however Ser. No. 13/912,318. However, further improvements have been made by the inventors. Though previous methods and devices are suitable for their intended purposes, the inventors have recognized problems in the art and have provided additional advances. Clustering as a concept is discussed below, partially repeated from in U.S. application Ser. No. 13/912,318 for completeness.

In at least one embodiment of the present disclosure, a collection system for automatically displaying patterns in a glucose data may include one or more processors, an electronic display and machine readable instructions. The electronic display can be communicatively coupled to the one or more processors. The machine readable instructions can be executed by the one or more processors. Further, the machine readable instructions can cause the one or more processors to: receive a glucose data signal indicative of ambulatory glucose levels sampled over time; divide the glucose data signal into segments of interest; transform, automatically, each of the segments of interest into a set of features according to a mathematical algorithm, and/or cluster, automatically, the segments of interest into groups of clustered segments according to a clustering algorithm. The segments of interest can be grouped in the groups of clustered segments based at least in part upon the set of features. A cluster center can be associated with one of the groups of clustered segments. The cluster center can be based upon a mean the one of the groups of clustered segments. The machine readable instructions can also cause the one or more processers to present, automatically, the cluster center on the electronic display.

In at least one embodiment of the present disclosure, a method for automatically displaying patterns in biological monitoring data is described that may include receiving biological data indicative of ambulatory biological information sampled over time from one or more subjects. The biological data may include a time index. Further, the biological data may be divided into segments of interest according to the time index. Each of the segments of interest can be transformed, automatically with one or more processors, into a set of features according to a mathematical algorithm. The segments of interest can be clustered, automatically with one or more processors, into groups of clustered segments according to a clustering algorithm. The clustering algorithm can calculate a distance metric based at least in part upon the set of features of each of the segments of interest such that similar segments of interest are grouped in one of the groups of clustered segments. The clustering algorithm can calculate a cluster center that is associated with one of the groups of clustered segments. The cluster center can be based upon a mean of the one of the groups of clustered segments. Moreover, the cluster center can be presented, automatically with the one or more processors, with a human machine interface.

The pattern enhancement algorithm generally enhances data patterns by clustering similar biological outcomes, i.e., glucose values, to identify the inputs that may have caused the biological response. The pattern enhancement algorithm comprises a process for receiving biological data indicative of ambulatory biological information sampled over time from one or more subjects. The biological data can include a time index that is suitable to associate the biological data.

The pattern enhancement algorithm comprises a process for clustering the segments of interest. Specifically, a clustering algorithm can be applied. The pattern enhancement algorithm comprises a process for clustering the segments of interest. Specifically, a clustering algorithm can be applied automatically to cluster the segments of interest into groups of clustered segments. Once clustered, similar segments of interest are grouped in each the clustered segments. Accordingly, the groups of clustered segments enhance and identify patterns that exist within the data. In some embodiments, the clustering algorithm can determine both the number of clusters and the segments of interest that are assigned to each cluster based upon the distance metric. The clustering algorithm used may include functions for determining the number of clusters such as, for example, a Schwarz Criterion, a Bayesian Information Criterion, an Akaike Information Criterion, or any other optimizer. The clustering algorithm used may include functions for assigning segments of interest to cluster such as, for example, K-means, Hierarchical clustering (using either an agglomerative or divisive method or some combination of both), Gaussian mixture modeling, Normalized Cuts, or other any clustering algorithm. It is noted, that the example described below utilizes for K-means clustering, but other clustering algorithms may be utilized without deviating from the scope of the present disclosure.

According to the embodiments described herein, the pattern enhancement algorithm may comprise a process for ranking the groups of clustered segments. In one embodiment, the groups of clustered segments can be associated with an importance ranking based on the number of segments in the group. The importance ranking can also be based upon the occurrence of an event such as, for example, hypoglycemia or hyperglycemia. For example, a group of clustered segments can be associated with a relatively high importance ranking, compared to other groups of clustered segments, when the group includes a larger number of clustered segments, which can be indicative of a common behavior, than the other groups and is coincident with one or more instances of hypoglycemic events or hyperglycemic events. A group of clustered segments associated with a relatively high importance ranking can be indicative of behavior that needs to be addressed by the health care professional or PwD. Accordingly, the groups of clustered segments clusters can be ranked based on the need for the HCP to adjust therapy or provide education to address the problem.

The pattern enhancement algorithm comprises a process for clustering the segments of interest. Specifically, a clustering algorithm can be applied automatically to cluster the segments of interest into groups of clustered segments. Once clustered, similar segments of interest can be grouped in each the clustered segments. Accordingly, the groups of clustered segments enhance and identify patterns that exist within the data. In some embodiments, the clustering algorithm can determine both the number of clusters and the segments of interest that are assigned to each cluster based upon the distance metric. The clustering algorithm used may include functions for determining the number of clusters such as, for example, a Schwarz Criterion, a Bayesian Information Criterion, an Akaike Information Criterion, or any other optimizer. The clustering algorithm used may include functions for assigning segments of interest to cluster such as, for example, K-means, Hierarchical clustering (using either an agglomerative or divisive method or some combination of both), Gaussian mixture modeling, Normalized Cuts, or other any clustering algorithm. It is noted, that the example described below utilizes for K-means clustering, but other clustering algorithms may be utilized without deviating from the scope of the present disclosure.

Summary statistics may also be calculated for each group of clustered segments and automatically displayed on the human machine interface by the one or more processors. The summary statistics may include the mean, median, standard deviation, mean absolute difference, range, quartiles or any other suitable statistics. The statistics may also include percentage of time in hyperglycemia, percentage of time within a target range, percentage of time below a threshold, or percentage of time above a specific threshold, for example. Summary statistics may also include parameters based on the number of groups that represent the biological data, the number of data segments in each group, or any other parameters related to the distribution of data segments within the groups of clustered segments. The summary statistics may be used as metrics to characterize the state of the PwD as well as indicators for potential therapy adjustments.

Additionally, regions of importance such as, for example, hyperglycemia, hypoglycemia, glucose target ranges, and the like can be displayed automatically on the human machine interface. For example, a hypoglycemia threshold and a target glucose concentration range can be displayed on the human machine interface. The human machine interface can also display contextual data associated with the clustered data segments such as, for example, meal tags, carbohydrate intake, insulin injections, or other relevant contextual data. The cluster centers can also be overlaid upon curves indicative of the clustered segments and/or the segments of interest.

A calendar can also be displayed by the human machine interface to identify weekly or monthly patterns. In one embodiment, the calendar can be coded to indicate the dates that correspond to cluster centers. Each code can be a color, a gradient, a shape, an alphanumeric, or any other visual indicator sufficient to distinguish the cluster code from other objects displayed by the human machine interface. Specifically, dates coded with a first cluster code include one or more clustered segments that correspond to the first cluster segment, dates coded with a second cluster code include one or more clustered segments that correspond to the second cluster center, dates coded with a third cluster code include one or more clustered segments that correspond to the first cluster segment, and dates coded with a fourth cluster code.

In a specific clustering example, a pattern enhancement algorithm can be executed by a processor to automatically group a CGM data indicative of ambulatory glucose levels sampled over time into groups of clustered segments. Filtered CGM data were received by the processor and segmented into segments of interest. Each segment of interest was selected to begin at 5:00 AM, so that the overnight data would remain continuous, and was of substantially equal length (about 24 hours). A set of features was extracted from each of the segments of interest. As a result, each of the segments of interest were compressed from vectors having a length of about 1440 (number of minutes in a day) into vectors having a length of about 20 by using the first 20 Eigenvectors.

The group of clustered segments can also be associated with dates to identify workday vs. non-workday, monthly or seasonally. Furthermore, the clustered segments can be aggregated based upon discrete data, for example, sensor production lot numbers, insulin lot numbers, or pump reusable lot numbers in order to help identify potential manufacturing defects.

As is noted above, once the patterns in the data are enhanced by generating clustered segments, the patterns in the biological data can automatically be displayed on a human machine interface by the one or more processors. The displayed clustered segments enhance the patterns that exist in the data and that may have been obscured. Accordingly, a user such as a HCP or a PwD can more readily identify patterns in the biological data.

Additionally, the mean of each group of clustered segments can be displayed automatically on the human machine interface. First, second, or third, or more cluster means for a first, second, third, or more clustered segments can be displayed.

Computation of Risk

As indicated earlier, the concept pertaining to the computation of risk and mapping of risk surface has been presented in U.S. application Ser. No. 13/645,198, "System and Method for Assessing Risk Associated with a Glucose State," however Ser. No. 13/912,318 does not discuss risk in the context of patterns. Though previous methods and devices are suitable for their intended purposes, the inventors have recognized problems in the art and have provided additional advances. Risk values as a concept is discussed below, partially repeated from in U.S. application Ser. No. 13/912,318 for completeness.

Biological monitoring provides health care providers (HCPs) and patients with biological data that can be utilized to treat and/or manage a medical condition related to the biological data. For example, CGM devices provide glucose data related to a detected level or concentration of glucose contained within the blood of people with diabetes (PwDs). Hazard metrics may be derived from glucose data for assessing a hazard to the diabetic person based on a detected glucose level. However, current hazard metrics often fail to account for the rate of change of the glucose data and the uncertainty of the accuracy of the glucose data. As such, current hazard metrics are often not appropriate to use as a metric for optimizing therapy or for evaluating the total amount of risk over a window of CGM measurements.

For example, a known hazard metric includes the hazard function illustrated in graph form in the following paper: Kovatchev, B. P. et al., *Symmetrization of the blood glucose measurement scale and its applications*, Diabetes Care, 1997, 20, 1655-1658. The Kovatchev hazard function is defined by the equation $h(g)=[1.509(\log(g)^{1.0804}-5.381)]^2$, wherein g is the blood glucose concentration (in milligrams per deciliter or mg/dl) shown on the x-axis and h(g) is the corresponding penalty value shown on the y-axis. The Kovatchev function provides a static penalty (i.e., hazard) value in that the penalty depends only on the glucose level. The minimum (zero) hazard occurs at 112.5 mg/dl. The hazard with the glucose level approaching hypoglycemia rises significantly faster than the hazard with the glucose level approaching hyperglycemia.

The Kovatchev hazard function fails to account for the rate of change of the glucose level as well as the uncertainty associated with the measured glucose level. For example, a patient's hazard associated with 100 mg/dl and a rapidly falling blood glucose level is likely greater than the patient's hazard associated with 100 mg/dl with a constant glucose rate of change. Further, measured glucose results from a glucose sensor may contain sensor noise, such as noise due to physical movement of the glucose sensor relative to the person's body or due to electrical noise inherent in the glucose sensor. Further, the glucose sensor may malfunction, such as due to electronics or battery failure or due to detachment or dropout of the sensor. As such, the measured glucose level may not be accurate. The penalty values provided with the Kovatchev function fail to account for such uncertainty in the measured glucose level.

Accordingly, some embodiments of the present disclosure provide risk metrics associated with measured CGM data that account for the blood glucose level, the rate of change of the blood glucose level, and/or the uncertainty associated with the blood glucose level and the rate of change. Further, some embodiments of the present disclosure calculate a target return path from a given glucose state to a target glucose state based on one or more risk or hazard metrics associated with intermediate glucose states of the target return path.

Based on the uncertainty associated with a detected glucose state, hazard analysis logic is operative to calculate a risk value for that detected glucose state. In particular, the risk value is equal to the cumulative penalty of the detected glucose state, as provided with matrix R, multiplied by the probability of accuracy of the measured glucose results as determined by logic. For a given cumulative penalty of a detected glucose state, the risk value calculated by logic increases with increasing uncertainty of the detected glucose state. The calculated risk value may be displayed on display of computing device. Further, the calculated risk value may be used to adjust therapy provided to the person with diabetes, such as adjusting an insulin bolus or basal rate, for example. For further description of the risk calculation functionality of computing device 66 as well as the probability distribution calculations, see U.S. patent application Ser. No. 12/818,795, filed on Jun. 18, 2010, entitled "Insulin Optimization Systems and Testing Methods with Adjusted Exit Criterion Accounting for System Noise Associated with Biomarkers," the entire disclosure of which is fully incorporated by reference herein.

A total penalty value J for a CGM trace may also be calculated with logic 80 based on the following equation:

$$J(g_{1...\tau}, dg_{1...\tau}) = \sum_{i=1}^{\tau} f_1(g_i, dg_i) + \mu f_2(g_\tau, dg_\tau) \quad (4)$$

wherein $f_1$ is the cumulative penalty of a given glucose state of the trace, $f_2$ is the cumulative penalty of the final glucose state of the trace, g is the glucose level, dg is the glucose rate of change, and μ is a parameter used to tune the balance between the cumulative penalty of the trace and the cumulative penalty of the final state. As such, the total penalty J of a CGM trace is the sum of the cumulative penalty for each point in the trace plus the cumulative penalty for the final state. Alternatively, $f_1$ and $f_2$ may be another penalty function described herein, such as the mean penalty rate or maximum cumulative penalty, or a combination of the penalty functions described herein.

In one embodiment, a target return path is calculated further based on a physiological limit of a glucose perturbation, such as a predetermined maximum acceleration, as described herein. In one embodiment, the logic unit calculates the target return path at block by identifying a plurality of potential glucose states ($GS_N$) based on the target glucose state, the physiological limit of the glucose perturbation (e.g., the assumed maximum acceleration), and a predetermined period. For example, the transition to the target glucose state from each of the potential glucose states is assumed by logic to be attainable by a person within the predetermined period based on the physiological limit.

In another exemplary method, a logic unit detects a glucose state of a person based on at least one measured glucose value provided with a glucose sensor. The logic unit determines a target return path for a transition from the detected glucose state to a target glucose state, as described herein. In one embodiment, the logic unit determines a target return path by identifying the glucose state in the lookup table that is nearest to the detected glucose state. The target return path associated with the identified nearest glucose state of the lookup table can then be identified as the target return path for the detected glucose state. The logic unit can compute at least one risk metric associated with the detected glucose state based on at least one intermediate glucose state of the target return path. In one embodiment, the at least one risk metric is computed by looking up the risk metric associated with the detected glucose state from the lookup table stored at memory. For example, the risk metric may include a cumulative penalty value, a total estimated time to return to the target glucose state from the detected glucose state, a mean penalty rate associated with the target return path, and a maximum penalty value associated with the target return path. In one embodiment the at least one risk metric is a cumulative risk value calculated by the logic unit, as described below.

In particular, the lookup table is further can be used to consider the uncertainty of a detected glucose state when analyzing the risk associated with the detected glucose state. In one embodiment, the logic unit calculates the risk associated with the detected glucose state and with all other glucose states of matrix R of the lookup table. The Logic unit then sums all of these individual risk values to determine a cumulative risk associated with the detected glucose state. For example, upon detecting a glucose state the logic unit can calculate the probability that the person is in that a specific glucose state. The logic unit further calculates the probability that the person is in each of the other glucose states of the penalty matrix R, such as based on the probability distribution of the detected glucose state described above. In one embodiment, calculating the probability of each glucose state includes calculating the probability or uncertainty of the glucose level and the probability or uncertainty of the glucose rate of change for each glucose state. Based on the probability calculations, the logic unit can then calculate the risk associated with each glucose state of matrix R, including the detected glucose state. Each risk value is computed based on the product of the probability measure and the corresponding cumulative penalty value of the glucose state. Finally, a logic unit can sum all of the computed risks of the glucose states of matrix R to determine a total or cumulative risk associated with the detected glucose state. The cumulative risk value may be stored in memory, may be presented to a user on display, and/or may be used for additional analyses or control strategies.

Alternatively, a logic unit may calculate the probability and associated risk for each of a subset of glucose states of matrix R (e.g., glucose states that are near the detected glucose state or are within a certain range of the probability distribution) rather than all glucose states of the matrix R. Further, the cumulative risk calculation may be calculated for other risk metrics, such as the risk metrics provided in the other penalty matrices described herein (E.g., matrix M, P, or T).

Based on a determined target return path for a detected glucose state of a person, various control strategies may be employed either by a computing device, by another system, or by human intervention. For example, a computing device may be in communication with a treatment system, such as an insulin therapy system or device. Based on the target return path and/or risk metric identified for the detected glucose state, the computing device can be operative to adjust, for example, a basal rate and/or bolus of an insulin treatment or another appropriate treatment to the person. For example, the insulin treatment may be adjusted such that the person's return towards the target glucose state substantially follows the target return path.

The risk metric values associated with the target return path for a detected glucose state may be undesirable or may exceed predefined limits, and thus treatment is adjusted such that a different return path towards the target glucose state is followed. For example, it may be desirable to avoid a maximum penalty value that is identified with the target return path for the detected glucose state due to the increased hazard or risk to the person that is associated with that penalty value. For example, the maximum penalty value may exceed a predetermined risk threshold identified for the person. As such, treatment may be adjusted such that the glucose state where the maximum penalty value occurs is avoided during the person's return towards the target glucose state. In this example, the therapy may be adjusted such that it follows a second return path that avoids the glucose state having the maximum penalty value.

Risk metrics for a glucose trace may be used retrospectively to analyze and draw inferences from behaviors of the person with diabetes and to identify and target areas of focus for the diabetes management. Behaviors may include meals, boluses, basal rates, exercise, hypo/hyper interventions, correction boluses, sleep, etc. Risk metrics such as the cumulative penalty and the mean penalty rate may be used to associate behaviors of the person with diabetes to an increase in the cumulative penalty or mean penalty rate to thereby identify behaviors that tend to result in increased levels of risk.

Alternative Methods to Direct Pattern Matching

One of the benefits of pattern matching is that it quickly enables a health care professional to assess what patterns occur most frequently within the patient's historical data. This analysis can be done to search for particular patterns such as post-prandial excursions after a meal. However using this approach by itself is cumbersome because if one searches for the most repeated patterns, then the result is not as insightful as it represents patterns that largely shown normal glycemia.

Identifying regions of problems requires one to know the problem first of all, i.e., hypoglycemia, or hyperglycemia. However, there is variation in these profiles owing to differences in: starting point of pattern in terms of glucose value, time at which the hypo event was initiated, or time bucket that includes the hypo event, and variability in the hyperglycemia peak, and what starting glucose value led to that peak. Consequently, assessing problem patterns can be a trial and error problem unless the events that one is looking for are tagged.

Therefore there has been a long-felt need in the art to find an approach to retrospectively analyze patterns of continuous monitoring in a way other than direct pattern matching, which has limitations as described. The inventors have found that by determining a risk score for a pattern, and comparing that to risk scores of patterns of data from data segments previously collected, a user/patient/health-care provider can have quick results that account for deficiencies in the prior art and allows a user patient/health-care provider to use collected data to determine how to change behavior to advantageously affect glucose levels. Applicants submit this is long-felt but unsolved need is objective evidence of non-obviousness that must be considered by the examiner in determining the issue of obviousness of claims for patentability under 35 U.S.C. 103 (MPEP 716.01(a)).

Figure 18:
FIG. 18 depicts an output plot showing patterns occurring most frequently.
Figure 18:
Figure 18:
Figure 18:
Figure 18:
Figure 19:
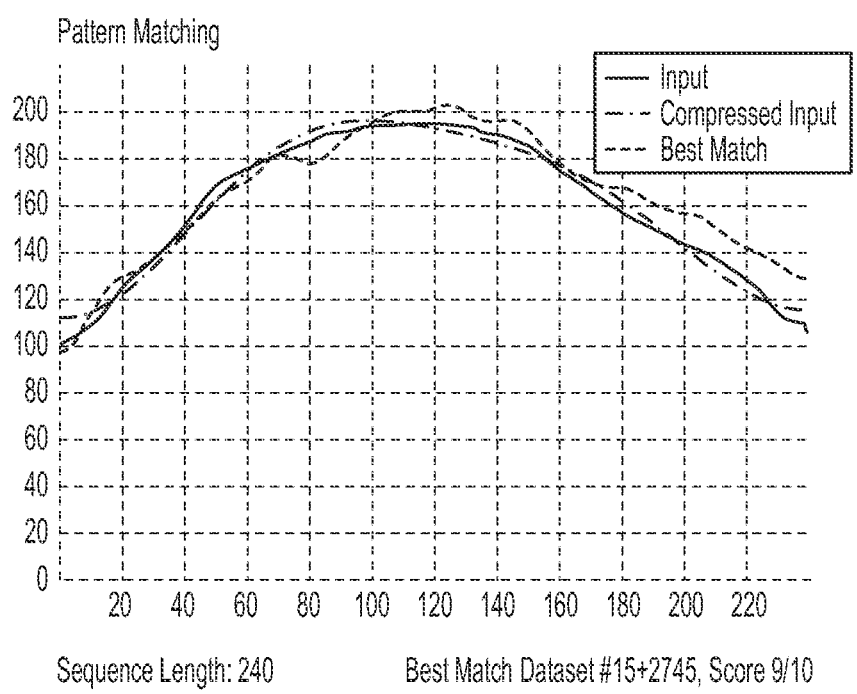
FIG. 19 shows a hyperglycemia match that exemplifies significant variability.

FIG. 18 shows a list of patterns that occur most frequently. Similarly, FIG. 19 shows a hyperglycemia match that exemplifies significant variability in terms of: where the peak occurs, initial range from where the start of the pattern starts (this pattern can also be observed for hypoglycemic patterns). FIG. 19 illustrates a pattern matching graph with lines of "Input," "Compressed Input," and "Best Match."

On account of these challenges, there is a need to find patterns based not on matches, but based on the risk posed by that pattern. One way to do this is to use a risk metric as outlined in U.S. patent application Ser. No. 13/645,198. In a specific embodiment, for example, as soon as data is stored in 4-hour segments a risk score is computed for that data-segment. Since one has the glucose values, and can compute the change in glucose this would not be difficult. All the segments in the database now have three markers associated with them: the actual data, the time of the data, and the hazard and/or risk score.

At the time of analysis, a doctor can either search for patterns as discussed in U.S. patent application Ser. No. 12/935,654, or he can look for patterns that represent most risk. These patterns can be found as follows: determine the patterns that represent the most risk overall, determine the time-window where the maximum number of patterns with high risk occur, compare the risk scores for given time intervals, i.e., post breakfast versus post lunch to determine what meal represents a higher risk. Additionally, this data will also be useful for the patient in real time as he could: look at tagged meals in the database to determine what their resultant risk scores were for the glucose response. This would help meal selection. The patient could assess his/her glucose levels at the present time to determine the possible risk outcome constitutes risk, a number of different metrics can be used such as the sum of the absolute risk scores or the maximum risk for a pattern.

Figure 20:
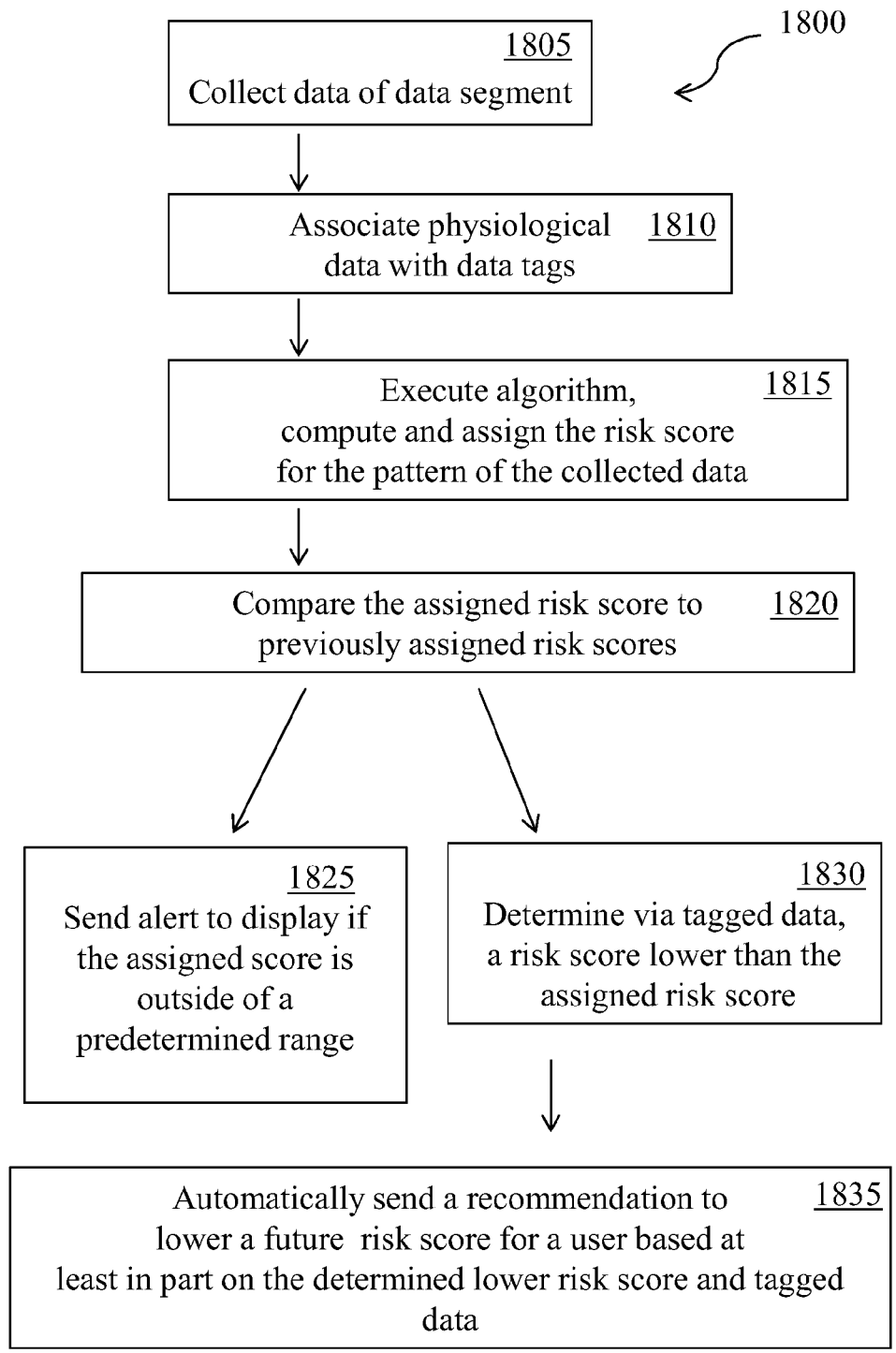
FIG. 20 depicts a flowchart of an exemplary risk score matching process using a patient monitoring system.

FIG. 20 depicts a flowchart 1800 of an exemplary risk score matching process using a patient monitoring system. Shown are: collect data of data segment 1805; associate physiological data with data tags 1810; execute algorithm to compute and assign the risk score for the pattern of the collected data 1815; compare the assigned risk score to previously assigned risk scores 1820; determine via tagged data a risk score lower than the assigned risk score 1830; automatically send a recommendation to lower a future risk score for a user based at least on part on the determined lower risk score and tagged data 1835; and send alert to display if the assigned risk score is outside a predetermined range 1825. In specific embodiments data associated with the data tags includes aspects of time for the data segment, start and end times, duration, etc.

In specific embodiments the device can access the patient/user medical history and take that into account in providing alerts or recommendations regarding future events/meals.

In specific embodiments, a device is provided that is a handheld device with a single button that can be pushed by the user/patient/medical personnel to cause the processor to execute the algorithm. In specific embodiments, the processor will cause an automatic display allowing the user/patient/medical personnel to select display of data segment data, or to select the format and timing for display of future data segment data. In a specific embodiment, the pushing of a button causes a risk score comparison, and by pressing the button again, a pattern matching is performed and each are displayed simultaneously or one after the other with a preprogrammed time of presentation; in another embodiment the risk score comparison and the pattern matching are performed with the pushing of separate buttons. A menu can be provided allowing a user/patient/medical personnel to select options on what will be automatically displayed after each collected data segment (if anything), and whether an automatic search should be performed after each data segment, via the algorithm by the processor, for a lowest risk score in memory (or for the comparable data segment of the same period on a previous day) and a recommended course of action for eating specific foods for a future data segment. In specific embodiments, the device, via this display, will depict a query once the button is pushed again, for what the user/patient/medical personnel would like to compare, and the/patient/medical personnel can respond by setting a comparison of data from data segments from the previous 4 hours as compared with the same four hours on any previous day for the past week, month, or year; the comparison can include risk scores or can include any tagged information from time collected to an event including meals or meal components ingested, calories of food, quantities, carbohydrate level, etc. In other embodiments the device can display averages of the data from the data segments for any previous data segment or specifically for the same time period as the most recently collected data segment but for a previous day (or averages of previous days such as 1-7 days or 1-30 days or 1-365 days). The user can request, in specific embodiments, a display information from tagging of the data of the data segment with the lowest risk score in memory, such as the previous day, week, month, or year; the displayed information can include meals or meal components ingested, calories of food, quantities, carbohydrate level, etc. The user/patient/medical personnel can then program a planned future meal via the processor using the same button or a separate button, and can request a reminder from the device, such that the device displays the planned meal just prior to the future data window for which the meal was planned. The programmer can also provide, via the hand-held device, an alarm, such as an audio, colorimetric, or vibrational alarm to notify the user/patient/medical personnel at the time for which the meal was programmed.

In specific embodiments the processor will cause the algorithm to immediately analyze a data segment data upon storage in memory, and compare the data to the programmed/planned meal, and to automatically display on the display of the hand-held device a note if the planned meal was not followed fully, or a note that it was not followed in-part with a detailed listing of the items not eaten, etc. and to automatically display a new planned meal to correct to account for the fact the planned meal was not eaten or was not eaten in part.

Embodiments provided herein account for differences in: starting point of pattern in terms of glucose value, time at which the hypo event was initiated, or time bucket that includes the hypo event, and variability in the hyperglycemia peak, and what starting glucose value led to that peak. In specific embodiments the database contains scores from data segments containing data with measurements of glucose values, wherein the risk scores for multiple data segments are stored in memory, and the scores account and allow comparison to newly assigned scores, wherein the scores are from data segments of different data segment starting times, total lengths, and wherein the glucose curves have different peak levels and in specific embodiments have been smoothed with smoothing software prior to comparison.

In specific non-limiting embodiments data segments can be 1, 2, 4, 6, 8, 10, or 24 hours long. In certain embodiments the data segments are 4-hours long the at least one data segment comprises at least six data segment segments such that at least a 24-hour period is analyzed In specific embodiments advice/recommendations are provided via the processor to the display, and the advice can include a change in activities or meals or meal components, and can be devised by recommending a course of action (known from tagging in the memory) mirroring the activities performed in a previous period where a data segment was collected, and the risk score was lower than the most recently determined risk score; in specific embodiments two or three or more recommendations can separately or simultaneously be presented to a user via the display; in specific embodiments the user/patient can interactively select a recommended course for following for a future data segment.

In specific embodiments comparing risk scores comprises tagging of data of the data segment at the time of storage, with information as to the daily period of time at which the data is collected, and is performed voluntarily by an action of a patient, who can press a button or otherwise set in motion the comparing of risk scores through a device, and the button can be pressed at any point when the patient feels hypoglycemic. The comparison can be made at random times, or can be performed multiple times, with the intervening times appearing random, such as based on the curiosity of the patient. The device can perform comparisons automatically at preprogrammed time intervals, and can also be designed to accept voluntary risk score comparison queries.

In specific embodiments one or more of the methods or devices, or both can be produced by or can herein include one or more of: wherein the data segments with the previously assigned risk scores comprise at least two data segments collected on different days from each other and the start of each of the at least two data segments was at different times from each other on each day, respectively, and the comparing the risk score to the previously assigned risk scores comprises comparing the risk score to the previously assigned risk score of each of the at least two data segments; wherein the data segments with the previously assigned risk scores include at least two data segments containing the data with different starting glucose levels from each other, and the comparing the risk score to the previously assigned risk scores comprises comparing the risk score to the previously assigned risk score of each of the at least two data segments; determining, via the algorithm, a course of action to increase the probability of decreasing a future risk score for a future data reference pattern of at least one future data segment to a level below the risk score computed for the data reference pattern of the data segment, and wherein the at least one future data segment is at least 24-hours from the time of start of when the data of the at least one data segment was collected; sending, via the processor to a display of a hand-held device, at least one recommendation for a change in meal components for the at least one future data segment to increase the probability of decreasing the future risk score for the future data reference pattern for the at least one future data segment to the level below the risk score computed for the data segment; sending, via the processor, an alert to a display of a hand-held device when the risk score is above a predetermined level; the memory storing the actual data, the time of the data, and the risk score; determining statistical probability for the risk score of going outside the predetermined glucose range and sending, via the processor, the statistical probability to a display of a hand-held device of to the patient; creating a series of ranges for risk scores, and providing an alert to medical personnel if the assigned risk score is within the predetermined range; tagging the data of the data segment at the time of storage, with information as to a daily period of time at which the data is collected, wherein the daily period of time is either before, during, or after a meal, and wherein comparing the risk score to the previously assigned risk scores comprises comparing the risk score of the reference pattern data with the previously assigned risk scores of the previously stored reference pattern data of the previously collected data segments from the same daily period of time as the data segment; comparing the risk score of the reference pattern data of the data segment with the previously assigned risk scores of the previously stored reference pattern data of the previously collected data segment comprises comparing at least two of the previously assigned risk scores of the reference pattern data of the previously collected data segments from the same daily period of time as the data segment and determining which has the lowest risk, and sending to the patient, via the processor to a display of a hand-held device, a message containing advice for a change in meal components for a future risk score of a future reference pattern data a future data segment; determining a daily period of time in a 24-hour period of time where the highest risk occurs for a given meal; the processor determining a strategy to lower the risk score for a future reference pattern data for a future data segment, and sending to the user, via the processor to a display of a computer, a recommended course to decrease the risk on the next day for the same daily period of time as the period of time in which the data of the at least one data segment was collected; the patient performing a self-analysis of at least a 24 hour period of time and changing plans for a future meal based at least in part on the risk score of the reference pattern data of the at least one data segment; collecting reference pattern data from at least two segments, and performing, via the processor, a second algorithm, clustering automatically, at least two data segments into groups of clustered segments according to a clustering algorithm, wherein segments of interest are grouped in the group of clustered segments, and wherein a cluster center is based upon a mean of one of the groups of clustered segments, and, present automatically the cluster center on an electronic display of the physiological data input device; wherein assigning the risk score for the reference pattern of the data of the at least one data segment comprises a calculation accounting for glucose rate of change; wherein the physiological data input device is a hand-held device; wherein the device is a personal digital assistant (PDA), a mobile phone, or a glucose meter.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

The invention claimed is:

1. A method for retrospectively assessing continuous monitoring reference pattern data to determine a risk of a patient glucose level measurement taken in at least one data segment being outside a predetermined range comprising:
   providing:
      a physiological data input device for acquiring data of the at least one data segment, wherein the data is in the form of at least one glucose level measurement;
      a controller in communication with the physiological data input device for generating a reference pattern from the data;
      a memory coupled to the physiological data input device and the controller for storing reference pattern data of the at least one data segment and for storing an algorithm to compute and assign a risk score for the reference pattern data of the at least one data segment and access a database containing previously stored reference pattern data of previously collected data segments with previously assigned risk scores;
      a processor in communication with the memory in order to execute the algorithm to compute and assign the risk score computed for the reference pattern data of the at least one data segment and access the database containing the previously collected data segment reference pattern data with the assigned risk scores;
   collecting the data of the at least one data segment;
   generating the reference pattern from the data;
   storing the reference pattern data;
   executing, via the processor, the algorithm to compute and assign the risk score for the reference pattern data of the at least one data segment; and
   comparing the risk score to the previously assigned risk scores of the reference pattern data of the previously acquired data segments for a patient for the retrospective assessment of the risk of the patient glucose level measurement taken in the at least one data segment being outside the predetermined range.

2. The method of claim 1 wherein the data segments with the previously assigned risk scores comprise at least two data segments collected on different days from each other and the start of each of the at least two data segments was at different times from each other on each day, respectively, and the comparing the risk score to the previously assigned risk scores comprises comparing the risk score to the previously assigned risk score of each of the at least two data segments.

3. The method of claim 1 wherein the data segments with the previously assigned risk scores include at least two data segments containing the data with different starting glucose levels from each other, and the comparing the risk score to the previously assigned risk scores comprises comparing the risk score to the previously assigned risk score of each of the at least two data segments.

4. The method of claim 1 further comprising determining, via the algorithm, a course of action to increase the probability of decreasing a future risk score for a future data reference pattern of at least one future data segment to a level below the risk score computed for the data reference pattern of the data segment, and wherein the at least one future data segment is at least 24-hours from the time of start of when the data of the at least one data segment was collected.

5. The method of claim 4 further comprising sending, via the processor to a display of a hand-held device, at least one recommendation for a change in meal components for the at least one future data segment to increase the probability of decreasing the future risk score for the future data reference pattern for the at least one future data segment to the level below the risk score computed for the data segment.

6. The method of claim 1 further comprising sending, via the processor, an alert to a display of a hand-held device when the risk score is above a predetermined level.

7. The method of claim 1 further comprising the memory storing the actual data, the time of the data, and the risk score.

8. The method of claim 1 further comprising determining statistical probability for the risk score of going outside the predetermined glucose range and sending, via the processor, the statistical probability to a display of a hand-held device of to the patient.

9. The method of claim 1 further comprising creating a series of ranges for risk scores, and providing an alert to medical personnel if the assigned risk score is within the predetermined range.

10. The method of claim 1 further comprising tagging the data of the data segment at the time of storage, with information as to a daily period of time at which the data is collected, wherein the daily period of time is either before, during, or after a meal, and wherein comparing the risk score to the previously assigned risk scores comprises comparing the risk score of the reference pattern data with the previously assigned risk scores of the previously stored reference pattern data of the previously collected data segments from the same daily period of time as the data segment.

11. The method of claim 1 wherein comparing the risk score of the reference pattern data of the data segment with the previously assigned risk scores of the previously stored reference pattern data of the previously collected data segment comprises comparing at least two of the previously assigned risk scores of the reference pattern data of the previously collected data segments from the same daily period of time as the data segment and determining which has the lowest risk, and sending to the patient, via the processor to a display of a hand-held device, a message containing advice for a change in meal components for a future risk score of a future reference pattern data a future data segment.

12. The method of claim 1 further comprising determining a daily period of time in a 24-hour period of time where the highest risk occurs for a given meal.

13. The method of claim 1 further comprising the processor determining a strategy to lower the risk score for a future reference pattern data for a future data segment, and sending to the user, via the processor to a display of a computer, a recommended course to decrease the risk on the next day for the same daily period of time as the period of time in which the data of the at least one data segment was collected.

14. The method of claim 13 further comprising the patient performing a self-analysis of at least a 24 hour period of time and changing plans for a future meal based at least in part on the risk score of the reference pattern data of the at least one data segment.

15. The method of claim 1 further comprising collecting reference pattern data from at least two segments, and performing, via the processor, a second algorithm, clustering automatically, at least two data segments into groups of clustered segments according to a clustering algorithm, wherein segments of interest are grouped in the group of clustered segments, and wherein a cluster center is based upon a mean of one of the groups of clustered segments, and, present automatically the cluster center on an electronic display of the physiological data input device.

16. The method of claim 1 wherein the assigning the risk score for the reference pattern of the data of the at least one data segment comprises a calculation accounting for glucose rate of change.

17. A method of risk quantification in one or more physiological reference pattern data of a subject to identify potential trouble spots in one or more regions of the reference pattern data where therapy change can be employed by a health care professional, said method comprising:
   providing:
      a physiological data input device for acquiring data of at least one data segment, wherein the data is in the form of at least one glucose level measurement;
      a controller in communication with the physiological data input device to for generating a reference pattern from the data;
      a memory coupled to the physiological data input device and the controller for storing reference pattern data of the at least one data segment and for storing an algorithm to compute and assign a risk score for the reference pattern data of the at least one data segment and access a database containing previously stored reference pattern data of previously collected data segments with previously assigned risk scores;
      a processor in communication with the memory to execute the algorithm to compute and to assign the risk score computed for the reference pattern data of the at least one data segment and access the database containing the previously collected data segment reference pattern data and the previously assigned risk scores;
   collecting, via the physiological data input device, the data in the at least one data segment obtained during continuous monitoring;
   generating, via the controller, the reference pattern of the data of the at least one data segment;
   storing, via the memory, the reference pattern data of the at least one data segment;
   executing, via the processor, the algorithm;
   assigning, via the algorithm, the risk score computed for the reference pattern data of the at least one data segment;
   accessing, via the algorithm, the database containing the stored reference pattern data with the previously assigned risk scores;
   comparing, via the algorithm, the risk score of the collected data of the at least one data segment with the previously assigned risk scores of the database;
   identifying, via the algorithm, the data segments stored in the database with the same risk score as the risk score computed for the reference pattern data of the at least one data segment for identification of the potential trouble spots in the one or more regions of the reference pattern data where the therapy change can be employed by the health care professional;
   sending the risk score computed for the reference pattern data of the data segment and a list of the identified data segments stored in the database with the same risk score as the risk score to the heath care professional.

18. A device for retrospectively assessing continuous monitoring reference patterns to determine a risk of a patient glucose level measurement taken in at least one data segment being outside a predetermined range comprising:
  a physiological data input device for acquiring data of the at least one data segment;
  a controller in communication with the physiological data input device to for generating a reference pattern from the data;
  a memory coupled to the physiological data input device and the controller for storing the reference pattern data of the at least one data segment; and
  a processor in communication with the memory and configured to execute an algorithm, stored in the memory, to assign a risk score computed for the reference pattern data of the at least one data segment and access a database containing stored reference pattern data with previously assigned risk scores to compare the risk score with the previously assigned risk scores and determine a therapy to decrease a future risk score.

19. The device of claim 18 wherein the physiological data input device is a hand-held device.

20. The method of claim 15 wherein the device is a personal digital assistant (PDA), a mobile phone, or a glucose meter.

* * * * *

UNITED STATES PATENT AND TRADEMARK OFFICE
CERTIFICATE OF CORRECTION

PATENT NO. : 9,465,917 B2
APPLICATION NO. : 14/291446
DATED : October 11, 2016
INVENTOR(S) : Abhishek Soni et al.

Page 1 of 1

It is certified that error appears in the above-identified patent and that said Letters Patent is hereby corrected as shown below:

In the Claims

Column 39, Claim 8, Line 24,
"of to the patient." should read
--to the patient.--;

Column 39, Claim 11, Line 50,
"future risk score of a future reference pattern data a future" should read
--future risk score of a future reference pattern data for a future--;

Column 40, Claim 17, Line 25,
"data input device to for generating a reference pat-" should read
--data input device for generating a reference pat- --; and Column 41, Claim 18, Line 10,
"input device to for generating a reference pattern from" should read
--input device for generating a reference pattern from--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*